US012552812B2

(12) United States Patent
Chen et al.

(10) Patent No.: US 12,552,812 B2
(45) Date of Patent: Feb. 17, 2026

(54) PYRIDONE MULTIPLE-MEMBERED RING DERIVATIVES AND USE THEREOF

(71) Applicant: PHAENO THERAPEUTICS CO., LTD., Zhejiang (CN)

(72) Inventors: Kevin X Chen, Shanghai (CN); Jian Xiong, Shanghai (CN); Jingjing Wang, Shanghai (CN); Guoping Hu, Shanghai (CN); Jinxin Liu, Shangha (CN); Yu Han, Shanghai (CN); Jian Li, Shanghai (CN); Shuhui Chen, Shanghai (CN)

(73) Assignee: PHAENO THERAPEUTICS CO., LTD. (CN)

( * ) Notice: Subject to any disclaimer, the term of this patent is extended or adjusted under 35 U.S.C. 154(b) by 391 days.

(21) Appl. No.: 18/271,162

(22) PCT Filed: Jan. 7, 2022

(86) PCT No.: PCT/CN2022/070733

§ 371 (c)(1),
(2) Date: Jul. 6, 2023

(87) PCT Pub. No.: WO2022/148434

PCT Pub. Date: Jul. 14, 2022

(65) Prior Publication Data

US 2024/0025921 A1 Jan. 25, 2024

(30) Foreign Application Priority Data

| | | |
|---|---|---|
| Jan. 8, 2021 | (CN) | 202110024885.9 |
| Mar. 11, 2021 | (CN) | 202110264686.5 |
| May 11, 2021 | (CN) | 202110513447.9 |

(51) Int. Cl.
*C07D 519/00* (2006.01)
*A61P 31/16* (2006.01)

(52) U.S. Cl.
CPC ............ *C07D 519/00* (2013.01); *A61P 31/16* (2018.01)

(58) Field of Classification Search
None
See application file for complete search history.

(56) References Cited

U.S. PATENT DOCUMENTS

| | | | |
|---|---|---|---|
| 2018/0118760 | A1 | 5/2018 | Kawai et al. |
| 2019/0169206 | A1 | 6/2019 | Kawai et al. |
| 2019/0224198 | A1 | 7/2019 | Lin et al. |
| 2020/0283454 | A1 | 9/2020 | Tang et al. |

FOREIGN PATENT DOCUMENTS

| | | | |
|---|---|---|---|
| CN | 107709321 | A | 2/2018 |
| CN | 109503625 | A | 3/2019 |
| CN | 109721615 | A | 5/2019 |
| CN | 110300753 | A | 10/2019 |
| CN | 110494141 | A | 11/2019 |
| CN | 111217810 | A | 6/2020 |
| CN | 111410661 | A | 7/2020 |
| JP | 2017-105750 | A | 6/2017 |
| JP | 2022-541404 | A | 9/2022 |
| WO | 2016175224 | A1 | 11/2016 |
| WO | 2018/030463 | A1 | 2/2018 |
| WO | 2020015669 | A1 | 1/2020 |
| WO | 2021007506 | A1 | 1/2021 |

OTHER PUBLICATIONS

International Searching Report issued in International Patent Application No. PCT/CN2022/070733, Apr. 6, 2022, 10 pages.
Written Opinion of the International Searching Authority issued in International Patent Application No. PCT/CN2022/070733, Apr. 6, 2022, 10 pages.
Chinese Patent Application No. 202110024885.9 (not published), 64 pages.
Abraham, G. M., et al., "Baloxavir: A Novel Antiviral Agent in the Treatment of Influenza", Clinical Infectious Diseases, vol. 71, No. 7, Oct. 2020, pp. 1790-1794.
Extended European Search Report and Search Opinion received for EP Application No. 22736595.4, mailed on Oct. 22, 2024, 7 pages.
International Search Report and Written Opinion received for PCT Patent Application No. PCT/CN2022/070733, mailed on Apr. 6, 2022, 20 pages (9 pages of English Translation and 11 pages of Original Document).
Office Action received for Japanese Patent Application No. 2023-541778, mailed on Aug. 13, 2024, 6 pages (4 pages of English Translation and 2 pages of Original Document).
Office Action received for Japanese Patent Application No. 2023-541778, mailed on Jul. 25, 2024, 39 pages (19 pages of English Translation and 20 pages of Original Document).

(Continued)

*Primary Examiner* — Samantha L Shterengarts
(74) *Attorney, Agent, or Firm* — Dilworth IP, LLC

(57) ABSTRACT

Provided are a class of pyridone multiple-membered ring derivatives and the use thereof. Specifically provided are a compound as represented by formula (VI) and a pharmaceutically acceptable salt thereof.

(VI)

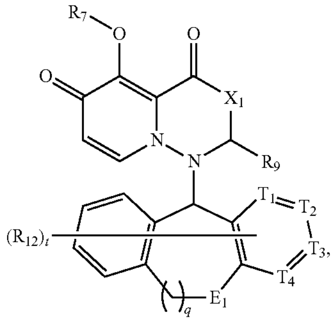

20 Claims, 4 Drawing Sheets

(56) References Cited

OTHER PUBLICATIONS

Pietka-Ottlik, M., et al., "Crucial Role of Selenium in the Virucidal Activity of Benzisoselenazol-3(2H)-ones and Related Diselenides", Molecules, vol. 15, No. 11, 2010 pp. 8214-8228.
First Office Action dated Mar. 14, 2024 issued in Australian Patent Application No. 2022205484.
May 1, 2025 1st Chinese Office Action issued in Chinese Patent Application No. CN202280009275.4.
Jul. 7, 2025 1st Korea Office Action issued in Korea Patent Application No. KR10-2023-7026759.

PYRIDONE MULTIPLE-MEMBERED RING DERIVATIVES AND USE THEREOF

CROSS-REFERENCE TO RELATED APPLICATIONS

The present application claims the right of the following priorities:

CN 202110024885.9, filed on Jan. 8, 2021;
CN 202110264686.5, filed on Mar. 11, 2021;
CN 202110513447.9, filed on May 11, 2021.

FIELD OF THE INVENTION

The present disclosure relates to a class of multiple fused ring derivatives of pyridone and a use thereof, specifically to a compound of formula (VI) and a pharmaceutically acceptable salt thereof.

BACKGROUND OF THE INVENTION

The epidemic influenza virus, also known as the influenza virus (IFV), is a segmented, single-stranded, negative-sense RNA virus that can cause epidemics of influenza in humans and animals. Influenza viruses can result in very high morbidity and mortality. Specifically, influenza A viruses can also cause global pandemics, such as the "Spanish Flu" (H1N1 subtype) from 1918 to 1920, the "Asian Flu" (H2N2 subtype) from 1957 to 1958, the "Asian Flu" (H3N2 subtype) from 1968 to 1969, the "Hong Kong Flu" (H1N1 subtype) from 1977 to 1978, and the H1N1 influenza that first broke out in Mexico in March 2009. An influenza pandemic can cause thousands of deaths, create widespread panic across societies and increased social instability.

Influenza A virus is a single-stranded, negative-sense RNA virus with a genome divided into 8 segments encoding eight proteins. The 5' and 3' ends of the influenza virus genome segment are highly conserved, and the sequences at the two ends are complementary, which allows them to form a stem-loop structure. This structure plays a vital role in initiating viral RNA replication. Each gene segment encodes proteins of varying sizes, and these segments each play different roles in the life cycle of the influenza virus. The basic functions of several major proteins are introduced as follows. The HA of the influenza virus serves as a ligand for recognizing host receptors. It binds to virus-specific receptors on the cell surface, mediates the fusion of the viral envelope with the intracellular vesicle membrane, and thereby releasing the viral nucleocapsid into the cytoplasm. The receptor of the influenza virus has specificity, and the receptor of the influenza A virus is a sialic acid glycoprotein. During the replication process, the NA protein of the influenza virus can remove sialic acid from the surface of the viral particles, preventing the virus particles from further clustering on the surface of host cells, facilitating the release of virions and further infection of more host cells.

The function of the M2 protein in the influenza virus: after the HA protein binds with sialic acid, the influenza virus is endocytosed by the host cell. The acidity and alkalinity in the phagosome play a crucial role in the uncoating of the virus. The ion channel of the M2 protein on the viral membrane gradually lowers the pH value of the phagosome. When the pH value drops to 5.0 to 6.0, there is a change in the HA2 protein conformation. The fusion peptide at the amino terminus of the HA2 protein shifts, thereby activating the fusion process. This shift results in the fusion of the virus's bilayer lipid membrane with the cell membrane, releasing the RNPs inside the viral particles into the host cell cytoplasm. The M2 protein, which is a transmembrane ion channel, is found exclusively in influenza A viruses. Part of this protein extends to the surface of the viral envelope.

The synthesis of the influenza virus protein also uses the translation mechanism in the host cell. Furthermore, the virus can suspend the translation of host protein and expedite the synthesis of its own protein. In the host cell, poly-adenylation of mRNA is achieved by a specific adenylate cyclase. In contrast, the adenylate tail of viral mRNA is formed by the transcription of 5 to 7 consecutive uracil on the negative-strand vRNA. The capping of various viral messenger RNAs (mRNAs) is performed in a similar manner: the PA and PB2 proteins snatch the 5' cap primer of the host pre-mRNA transcripts and subsequently initiate viral mRNA synthesis. This process, known as "cap snatching", is primarily carried out by the viral RNA-dependent RNA polymerase (RdRp). The PA subunit of RdRp, which has RNA endonuclease activity, is responsible for cleaving the host mRNA. Upon the completion of polyadenylation and capping, the viral mRNA is exported from the nucleus to the cytoplasm, where it is translated in the same manner as the host cell's mRNA. The nuclear export of viral vRNA fragments is mediated by the viral M1 and NS2 proteins. The M1 protein can interact with vRNA and the NP protein, and it also interacts with the nuclear export protein NS2. As a result, the nuclear export protein NS2 mediates the exit of the M1-RNP from the nucleus in the form of a nucleoprotein and enables its entry into the cytoplasm of the host cell.

Influenza results in direct costs related to lost productivity and the use of medical resources, as well as indirect costs associated with preventive measures. In the United States, the annual loss caused by influenza amounts to approximately $10 billion, and it is estimated that future influenza pandemics could incur hundreds of billions of dollars in direct and indirect costs. Moreover, the cost of prevention is very high, with governments worldwide having spent billions of dollars in preparation and planning for a potential H5N1 avian influenza pandemic. The preventive expenses are associated with the purchase of drugs and vaccines, as well as the development of strategies for disaster drills and enhanced border control.

The current options for influenza treatment include vaccination and the use of antiviral drugs for chemotherapy and chemoprophylaxis. Influenza vaccines are typically recommended for high-risk groups, such as children, the elderly, and individuals with conditions like asthma, diabetes, or heart disease. However, even with vaccination, it is not possible to entirely eliminate the risk of contracting influenza. Each season, new vaccines for specific influenza strains are developed. Still it is not possible to cover all the various virus strains actively infecting people worldwide during a given season. Moreover, due to a certain extent of antigenic drift in influenza viruses, if a single cell is infected by more than one strain, the eight individual vRNA segments in the genome may undergo a process of mixing or reassortment. This can lead to rapid genetic changes in the virus that may result in antigenic shifts, allowing the virus to infect new host species and swiftly bypass protective immunity.

Antiviral drugs can also be used to treat influenza, wherein neuraminidase inhibitors such as oseltamivir (Tamiflu), have significant effects on influenza A virus. However, clinical observations have identified the emergence of viral strains resistant to this class of neuraminidase inhibitors. In the field of anti-influenza virus, there is an urgent clinical need for anti-influenza virus drugs with a novel mechanism of action (MoA), which can be utilized in monotherapy, or in combination with other commercially available anti-influenza virus drugs with different MoAs, for the prevention and treatment of influenza A. In WO2016175224, RNA polymerase PA subunit inhibitors, such as S-033447 and its prodrug S-033188, are reported.

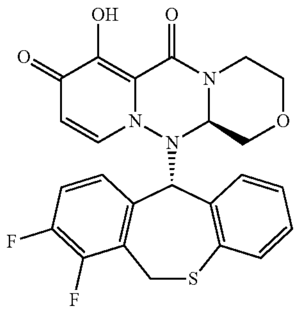

S-033447
Baloxavir

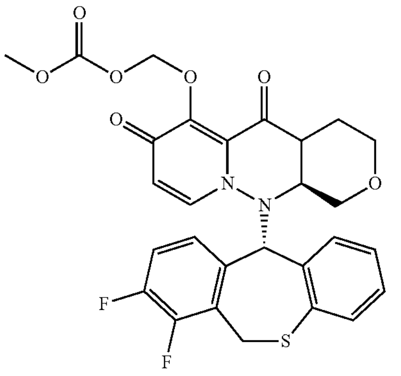

S-033188
Prodrug: Baloxavir marboxil

SUMMARY OF THE INVENTION

The present disclosure provides a compound of formula (VI) or a pharmaceutically acceptable salt thereof, (VI)

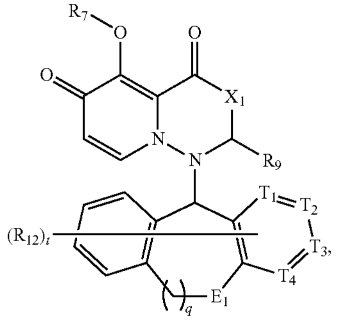

wherein $R_7$ is selected from H and

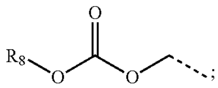
;

$R_8$ is selected from $C_{1-3}$ alkyl and

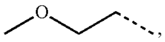
, and the $C_{1-3}$ alkyl and

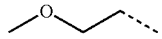

are optionally substituted by 1, 2, or 3 $R_a$;

$R_9$ is selected from H, $E_1$ is selected from Se, $X_1$ is selected from $CR_{10}R_{11}$, and $R_{10}$ and $R_{11}$ together with the atom to which they are commonly connected form a $C_{3-5}$ cycloalkyl group;

alternatively, $X_1$ and $R_9$ together with the atom to which they are connected form

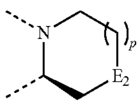
, p is selected from 0 and 1, one of $E_1$ and $E_2$ is selected from Se, and the other is selected from S and O;

$R_{12}$ is selected from H, F, Cl, Br, I, OH, $NH_2$, —COOH, $C_{1-3}$ alkyl, $C_{1-3}$ alkoxy, and $C_{1-3}$ alkylamino, and the $C_{1-3}$ alkyl, $C_{1-3}$ alkoxy, and $C_{1-3}$ alkylamino are each independently and optionally substituted by 1, 2, or 3 $R_b$;

$T_1$, $T_2$, $T_3$, and $T_4$ are each independently selected from CH and N;

q is selected from 0 and 1;

t is selected from 0, 1, 2, 3, and 4;

each $R_a$ and $R_b$ is independently selected from H, F, Cl, Br, and I;

provided that when $T_1$ is selected from CH, $E_1$ is selected from Se, $E_2$ is selected from O, p is selected from 1, and q is selected from 1, each $R_{12}$ is independently selected from OH and $NH_2$.

In some embodiments of the present disclosure, the each $R_{12}$ is independently selected from F, and other variables are as defined in the present disclosure.

In some embodiments of the present disclosure, the $R_8$ is selected from $CH_3$, $CH_2CH_3$, $CH_2CH_2CH_3$, $CH(CH_3)_2$, and

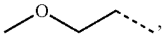
, and the $CH_3$, $CH_2CH_3$, $CH_2CH_2CH_3$, $CH(CH_3)_2$, and

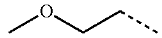

are optionally substituted by 1, 2, or 3 $R_a$, and other variables are as defined in the present disclosure.

In some embodiments of the present disclosure, the $R_8$ is selected from $CH_3$, $CH_2CH_3$, $CH(CH_3)_2$, and

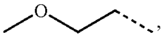, and other variables are as defined in the present disclosure.

In some embodiments of the present disclosure, the $R_8$ is selected from $CH_3$ and

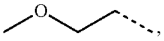, and other variables are as defined in the present disclosure.

In some embodiments of the present disclosure, the $R_7$ is selected from H,

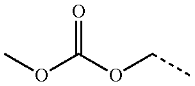, 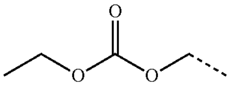, 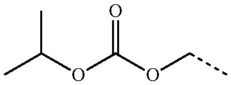, and 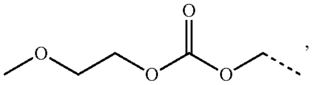, and other variables are as defined in the present disclosure.

In some embodiments of the present disclosure, the $R_7$ is selected from H,

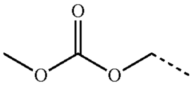, and 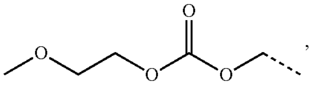, and other variables are as defined in the present disclosure.

In some embodiments of the present disclosure, the $R_7$ is selected from H and

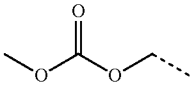, and other variables are as defined in the present disclosure.

In some embodiments of the present disclosure, the $E_1$ is selected from Se, $E_2$ is selected from O, and other variables are as defined in the present disclosure.

In some embodiments of the present disclosure, the structural moiety

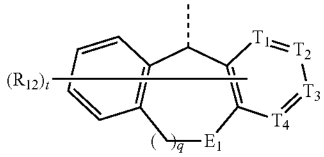

is selected from

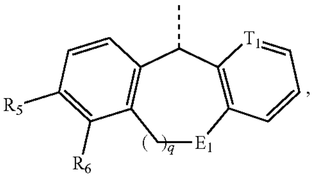, $R_5$ and $R_6$ are each independently selected from H, F, Cl, Br, I, OH, $NH_2$, —COOH, $C_{1-3}$ alkyl, $C_{1-3}$ alkoxy, and $C_{1-3}$ alkylamino, and the $C_{1-3}$ alkyl, $C_{1-3}$ alkoxy, and $C_{1-3}$ alkylamino are each independently and optionally substituted by 1, 2, or 3 $R_b$, and other variables are as defined in the present disclosure.

In some embodiments of the present disclosure, the structural moiety

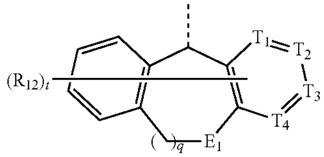

is selected from

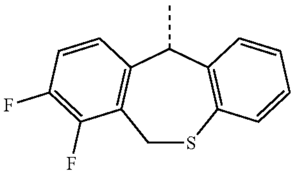,

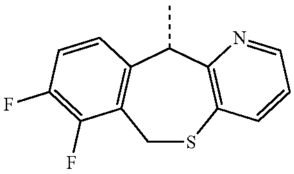,

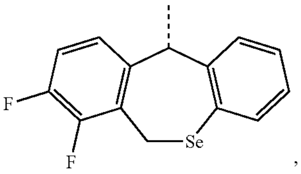, and

-continued

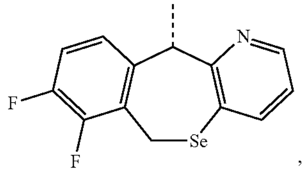 [SMILES: C[C@H]1c2ccc(F)c(F)c2C[Se]c2cccnc21]
, and other variables are as defined in the present disclosure.

In some embodiments of the present disclosure, the structural moiety

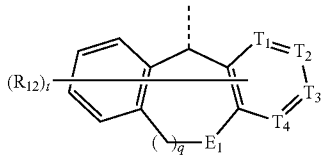

is selected from

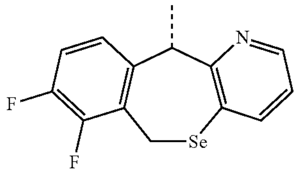
, and other variables are as defined in the present disclosure.

In some embodiments of the present disclosure, the $R_5$ is selected from F, and other variables are as defined in the present disclosure.

In some embodiments of the present disclosure, the $R_6$ is selected from F, and other variables are as defined in the present disclosure.

In some embodiments of the present disclosure, the structural moiety

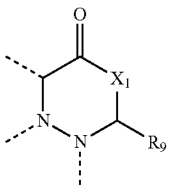

is selected from

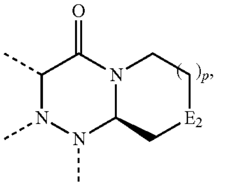
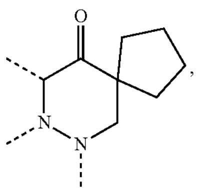
,

-continued

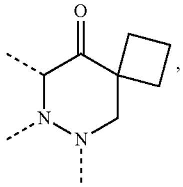
, and
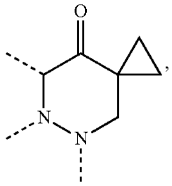
, and other variables are as defined in the present disclosure.

In some embodiments of the present disclosure, the structural moiety

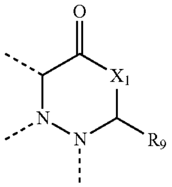

is selected from

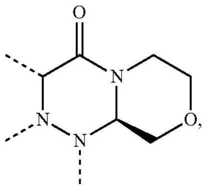
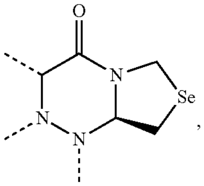
,
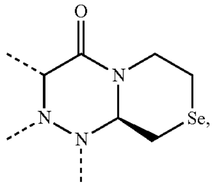
and
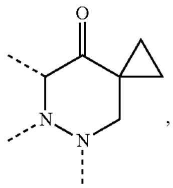
, and other variables are as defined in the present disclosure.

In some embodiments of the present disclosure, the structural moiety

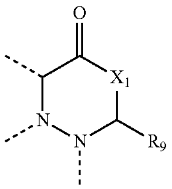

is selected from

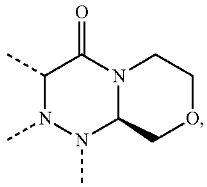

and other variables are as defined in the present disclosure.

In some embodiments of the present disclosure, the compound or the pharmaceutically acceptable salt thereof is selected from, (V)

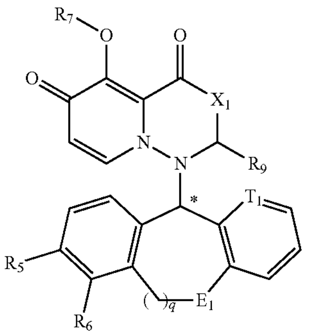

wherein $R_5$ and $R_6$ are each independently selected from H, F, Cl, Br, I, OH, and $NH_2$;

$R_7$ is selected from H and

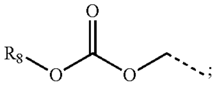

$R_8$ is selected from $C_{1-3}$ alkyl and

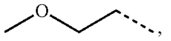

and the $C_{1-3}$ alkyl and

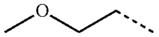

are optionally substituted by 1, 2, or 3 $R_a$;

$R_9$ is selected from H, $E_1$ is selected from Se, $X_1$ is selected from $CR_{10}R_{11}$, and $R_{10}$ and $R_{11}$ together with the atom to which they are commonly connected form the $C_{3-5}$ cycloalkyl group;

alternatively, $X_1$ and $R_9$ together with the atom to which they are connected form

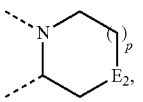

one of $E_1$ and $E_2$ is selected from Se, and the other is selected from S and O;

$T_1$ is selected from CH and N;

p and q are each independently selected from 0 and 1;

each $R_a$ is independently selected from H, F, Cl, Br, and I;

provided that when $T_1$ is selected from CH, $E_1$ is selected from Se, $E_2$ is selected from O, p is selected from 1, and q is selected from 1, $R_5$ and $R_6$ are each independently selected from OH and $NH_2$;

the carbon atom with "*" is a chiral carbon atom, which exists in the form of (R) or (S) single enantiomer or in an enantiomer-enriched form.

In some embodiments of the present disclosure, the compound or the pharmaceutically acceptable salt thereof is selected from, (IV)

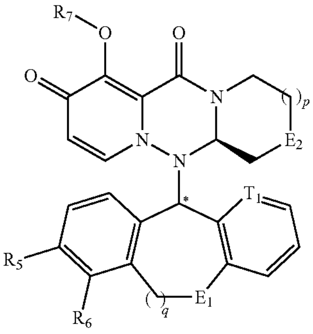

and (V-I)

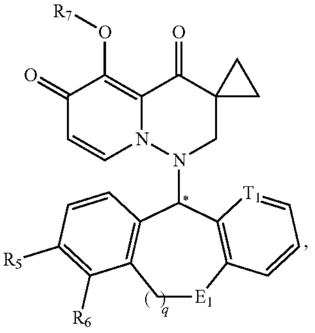

wherein p, q, $E_1$, $E_2$, $T_1$, $R_5$, $R_6$, and $R_7$ are as defined in the present disclosure;

the carbon atom with "*" is a chiral carbon atom, which exists in the form of (R) or (S) single enantiomer or in an enantiomer-enriched form.

In some embodiments of the present disclosure, the compound or the pharmaceutically acceptable salt thereof is selected from, (IV-A)

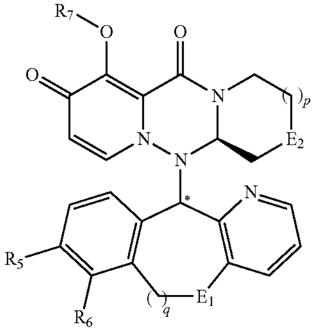

and

-continued (V-A)

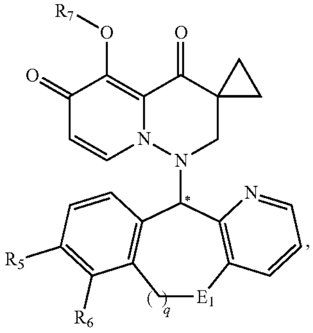, wherein p, q, $E_1$, $E_2$, $R_5$, $R_6$, and $R_7$ are as defined in the present disclosure;

the carbon atom with "*" is a chiral carbon atom, which exists in the form of (R) or (S) single enantiomer or in an enantiomer-enriched form.

In some embodiments of the present disclosure, the compound or the pharmaceutically acceptable salt thereof is selected from, (IV-A)

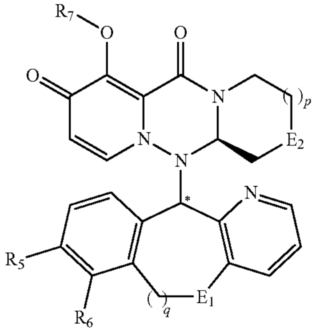

and (V-I-A)

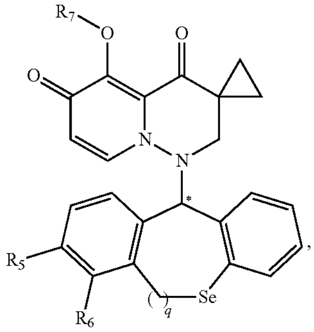, wherein p, q, $E_1$, $E_2$, $R_5$, $R_6$, and $R_7$ are as defined in the present disclosure;

the carbon atom with "*" is a chiral carbon atom, which exists in the form of (R) or (S) single enantiomer or in an enantiomer-enriched form.

In some embodiments of the present disclosure, the compound or the pharmaceutically acceptable salt thereof is selected from, (III-1)

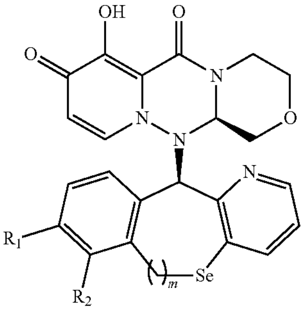

(III-2)

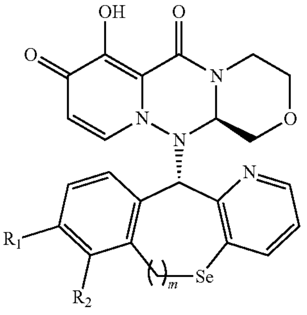

(IV-1)

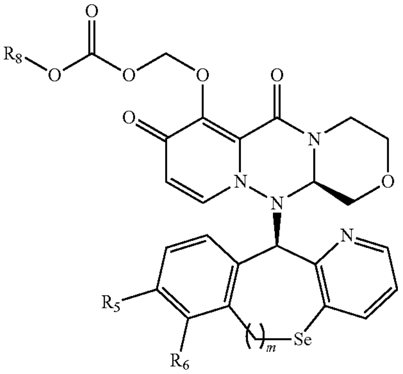

(IV-2)

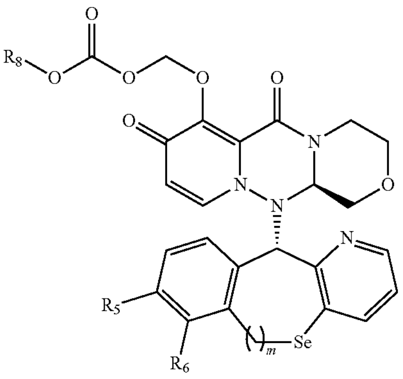

-continued (V-A-1)

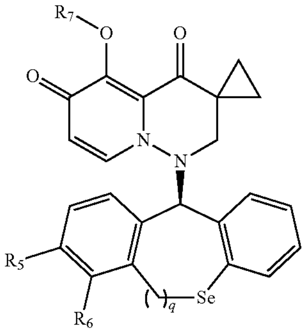

and (V-A-2)

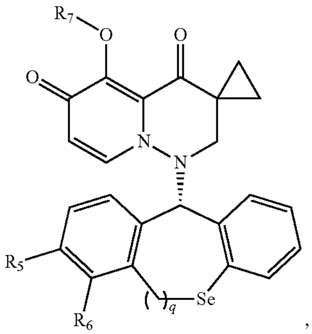

, wherein $R_1$ and $R_2$ are each independently selected from H, F, Cl, Br, I, OH, and $NH_2$;

m is selected from 0 and 1;

q, $R_5$, $R_6$, $R_7$, and $R_8$ are as defined in the present disclosure.

In some embodiments of the present disclosure, the $R_1$ and $R_2$ are each independently selected from F, and other variables are as defined in the present disclosure.

In some embodiments of the present disclosure, the $R_5$ and $R_6$ are each independently selected from F, and other variables are as defined in the present disclosure.

In some embodiments of the present disclosure, the compound or the pharmaceutically acceptable salt thereof is selected from, (III-1a)

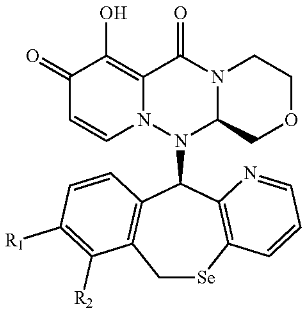

-continued (III-1b)

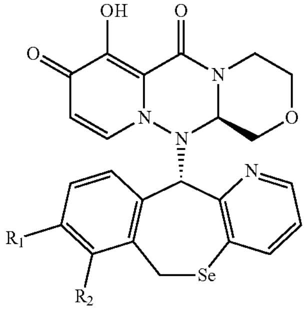

(IV-1a)

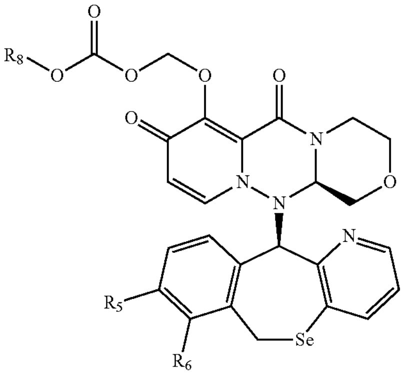

(IV-1b)

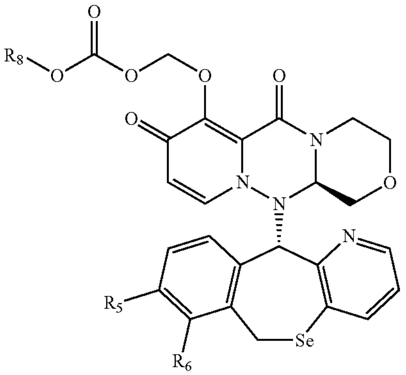

(V-1a)

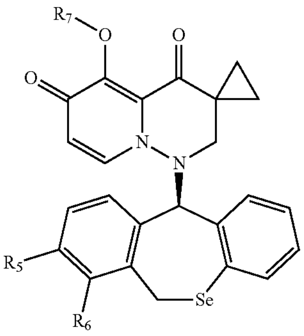

and

-continued
(V-1b)
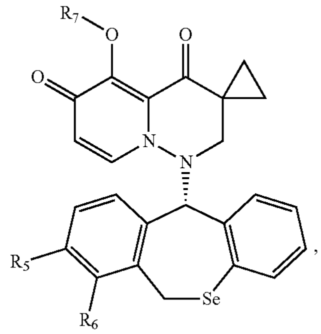
wherein $R_1$, $R_2$, $R_5$, $R_6$, $R_7$, and $R_8$ are as defined in the present disclosure.
In some embodiments of the present disclosure, the compound or the pharmaceutically acceptable salt thereof is selected from,
(I-1)
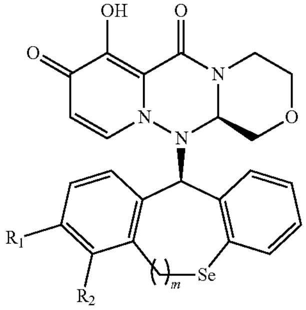
(I-2)
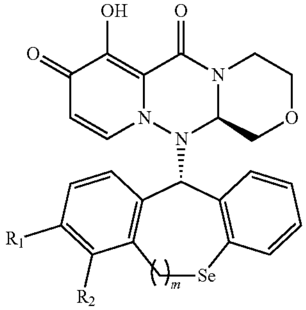
(II-1)
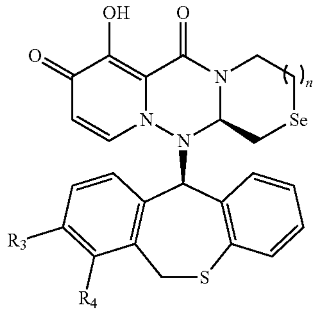
-continued
(II-2)
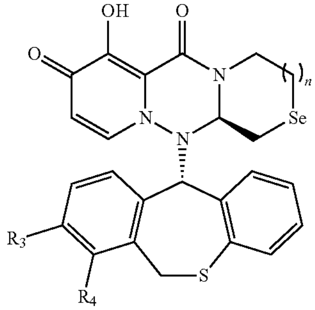
(III-1)
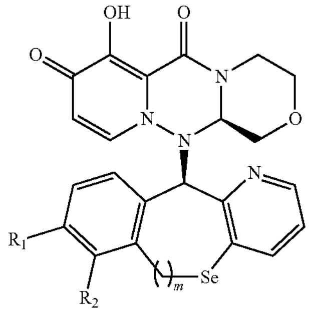
(III-2)
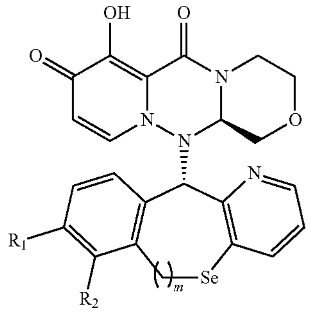
(IV-1)
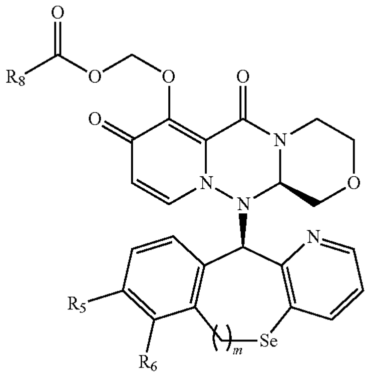

-continued (IV-2)

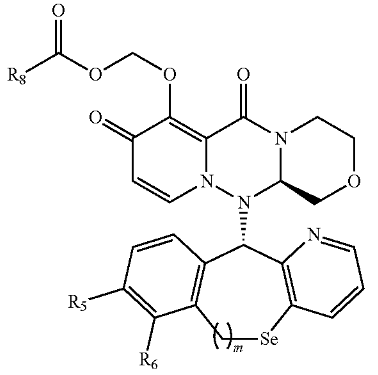

(V-A-1)

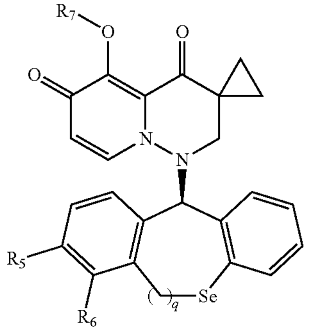

and (V-A-2)

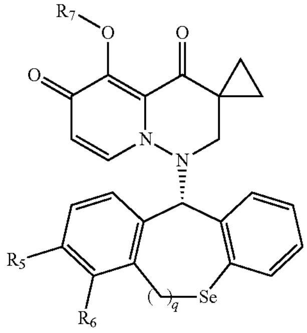

, wherein $R_1$, $R_2$, $R_3$, and $R_4$ are each independently selected from H, F, Cl, Br, I, OH, and $NH_2$;

n and m are each independently selected from 0 and 1;

provided that in formulas (I-1) and (I-2), when m is selected from 1, $R_1$ and $R_2$ are each independently selected from OH and $NH_2$;

q, $R_5$, $R_6$, and $R_8$ are as defined in the present disclosure.

In some embodiments of the present disclosure, the $R_1$ and $R_2$ are each independently selected from F, and other variables are as defined in the present disclosure.

In some embodiments of the present disclosure, the $R_3$ and $R_4$ are each independently selected from F, and other variables are as defined in the present disclosure.

In some embodiments of the present disclosure, the compound or the pharmaceutically acceptable salt thereof is selected from, (I-1a)

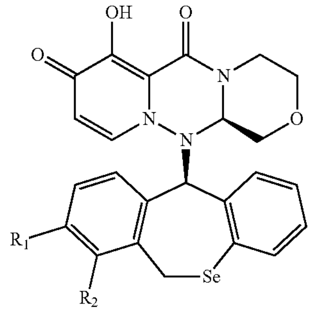

(I-1b)

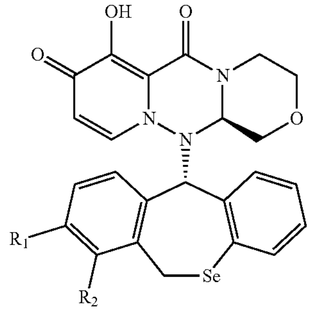

(I-2a)

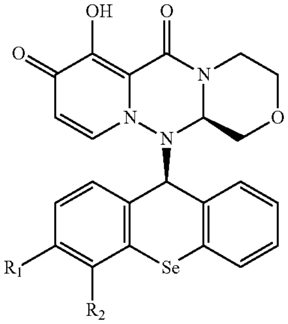

(I-2b)

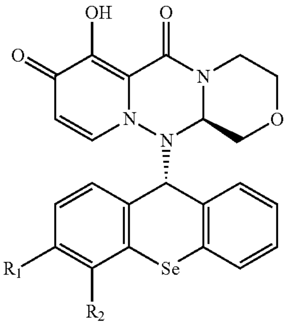

(II-1a)

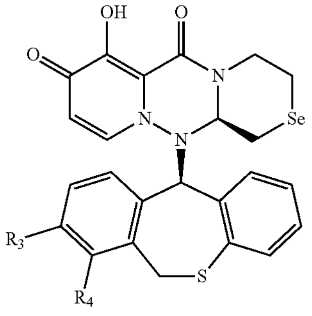

-continued
(II-1b)
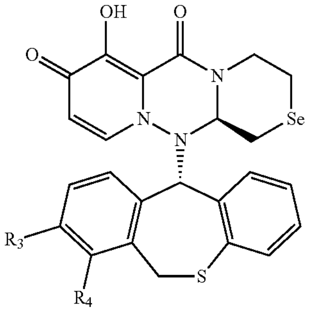
(II-2a)
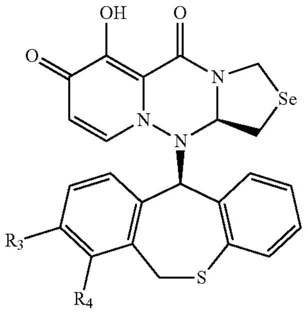
(II-2b)
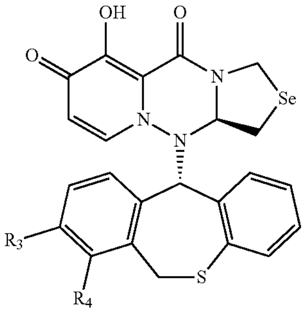
(III-1a)
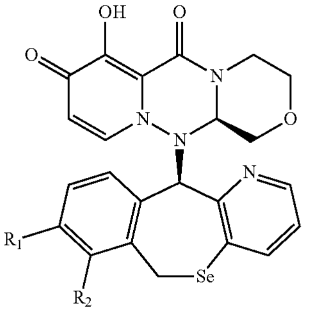
(III-1b)
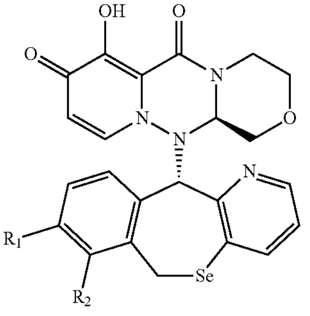
-continued
(III-2a)
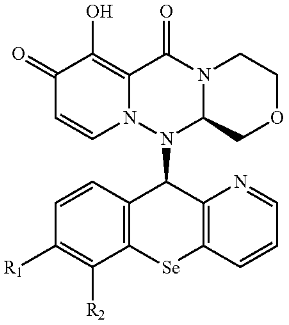
(III-2b)
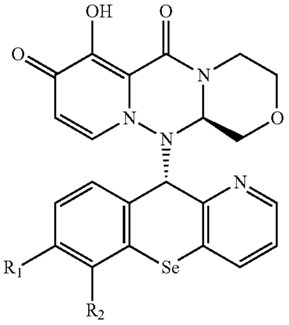
(IV-1a)
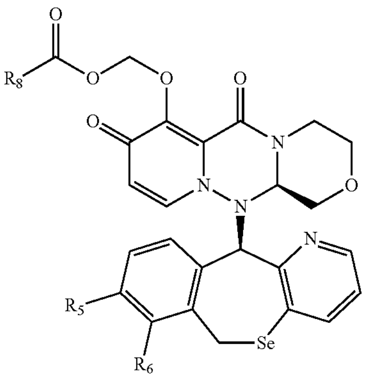
(IV-1b)
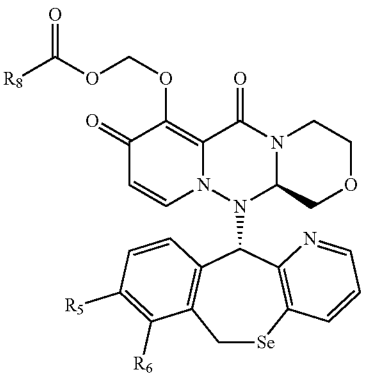

-continued
(IV-2a)
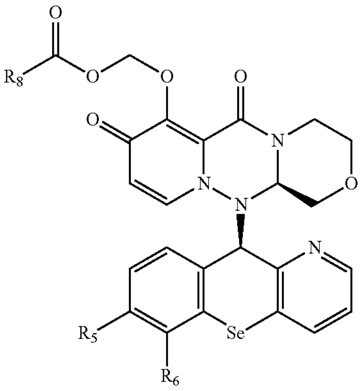
(IV-2b)
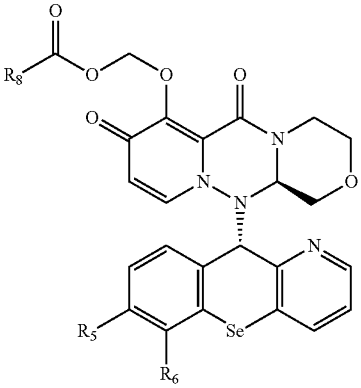
(V-1a)
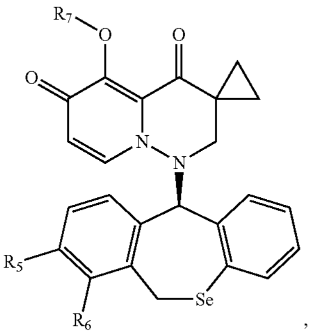
,
(V-1b)
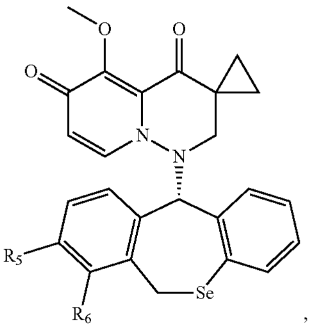
,
-continued
(V-2a)
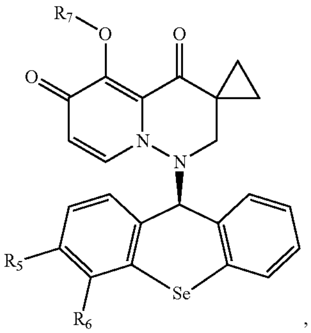
, and
(V-2b)
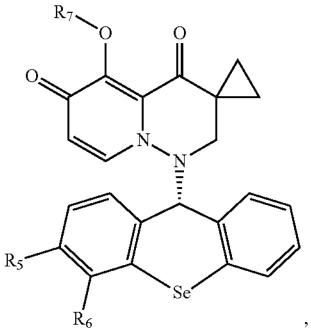
,
wherein
$R_1$, $R_2$, $R_3$, $R_4$, $R_5$, $R_6$, $R_7$, and $R_8$ are as defined in the present disclosure.
The present disclosure provides a compound of formula (V) or a pharmaceutically acceptable salt thereof,
(V)
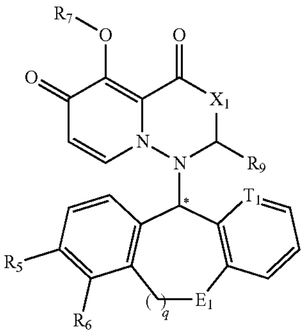
wherein
$R_5$ and $R_6$ are each independently selected from H, F, Cl, Br, I, OH, and $NH_2$;
$R_7$ is selected from H and
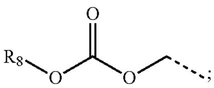
;

$R_8$ is selected from $C_{1-3}$ alkyl and

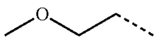

and the $C_{1-3}$ alkyl and

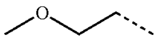

are optionally substituted by 1, 2, or 3 $R_a$;

$R_9$ is selected from H;

$X_1$ is selected from $CR_{10}R_{11}$, and $R_{10}$ and Ru together with the atom to which they are commonly connected form a $C_{3-5}$ cycloalkyl group;

alternatively, $X_1$ and $R_9$ are connected together to form

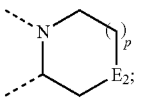

$E_1$ selected from S and Se;

$E_2$ is selected from O and Se, and at least one of $E_1$ and $E_2$ is selected from Se;

$T_1$ is selected from CH and N;

p and q are each independently selected from 0 and 1;

each $R_a$ is independently selected from H, F, Cl, Br, and I;

provided that when $T_1$ is selected from CH, $E_1$ is selected from Se, $E_2$ is selected from O, p is selected from 1, and q is selected from 1, $R_5$ and $R_6$ are each independently selected from OH and $NH_2$;

the carbon atom with "*" is a chiral carbon atom, which exists in the form of (R) or (S) single enantiomer or in an enantiomer-enriched form.

The present disclosure provides a compound of formula (IV) or a pharmaceutically acceptable salt thereof, (IV)

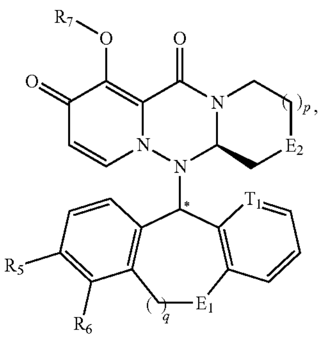

wherein $T_1$ is selected from CH and N;

$E_1$ selected from S and Se;

$E_2$ is selected from O and Se, and at least one of $E_1$ and $E_2$ is selected from Se;

$R_5$ and $R_6$ are each independently selected from H, F, Cl, Br, I, OH, and $NH_2$;

$R_7$ is selected from H and

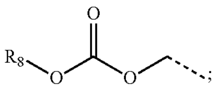

$R_8$ is selected from $C_{1-3}$ alkyl and

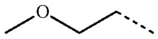

and the $C_{1-3}$ alkyl and

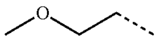

are optionally substituted by 1, 2, or 3 $R_a$;

p and q are each independently selected from 0 and 1;

each $R_a$ is independently selected from H, F, Cl, Br, and I;

provided that when $T_1$ is selected from CH, $E_1$ is selected from Se, $E_2$ is selected from O, p is selected from 1, and q is selected from 1, $R_5$ and $R_6$ are each independently selected from OH and $NH_2$;

the carbon atom with "*" is a chiral carbon atom, which exists in the form of (R) or (S) single enantiomer or in an enantiomer-enriched form.

In some embodiments of the present disclosure, the compound or the pharmaceutically acceptable salt thereof is selected from, (IV-A)

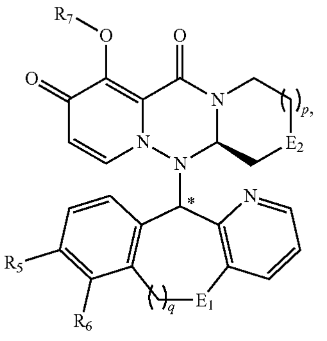

wherein p, q, $E_1$, $E_2$, $R_5$, $R_6$, and $R_7$ are as defined in the present disclosure;

the carbon atom with "*" is a chiral carbon atom, which exists in the form of (R) or (S) single enantiomer or in an enantiomer-enriched form.

The present disclosure provides a compound of formula (III) or a pharmaceutically acceptable salt thereof, (III)

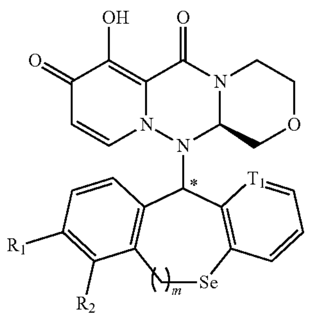

wherein $T_1$ is selected from CH and N;

$R_1$ is selected from H, F, Cl, Br, I, OH, and $NH_2$;

$R_2$ is selected from H, F, Cl, Br, I, OH, and $NH_2$;

m is selected from 0 and 1;

the carbon atom with "*" is a chiral carbon atom, which exists in the form of (R) or (S) single enantiomer or in an enantiomer-enriched form.

The present disclosure provides a compound of formula (II) or a pharmaceutically acceptable salt thereof, (II)

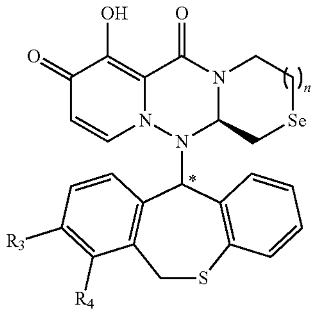

wherein $R_3$ is selected from H, F, Cl, Br, I, OH, and $NH_2$;

$R_4$ is selected from H, F, Cl, Br, I, OH, and $NH_2$;

n is selected from 0 and 1;

the carbon atom with "*" is a chiral carbon atom, which exists in the form of (R) or (S) single enantiomer or in an enantiomer-enriched form.

The present disclosure provides a compound of formula (I) or a pharmaceutically acceptable salt thereof, (I)

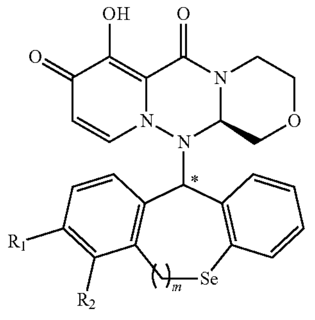

wherein $R_1$, $R_2$, and m are as defined in the present disclosure.

The present disclosure provides a compound of formula (I) or a pharmaceutically acceptable salt thereof, (I)

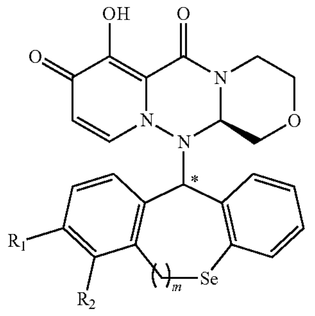

wherein $R_1$ is selected from H, F, Cl, Br, I, OH, and $NH_2$;

$R_2$ is selected from H, F, Cl, Br, I, OH, and $NH_2$;

m is selected from 0 and 1;

the carbon atom with "*" is a chiral carbon atom, which exists in the form of (R) or (S) single enantiomer or in an enantiomer-enriched form.

In some embodiments of the present disclosure, the $R_1$ is selected from F, and other variables are as defined in the present disclosure.

In some embodiments of the present disclosure, the $R_2$ is selected from F, and other variables are as defined in the present disclosure.

In some embodiments of the present disclosure, the $R_3$ is selected from F, and other variables are as defined in the present disclosure.

In some embodiments of the present disclosure, the $R_4$ is selected from F, and other variables are as defined in the present disclosure.

There are still some embodiments of the present disclosure which are obtained by any combination of the above variables.

The present disclosure provides a compound of the following formula or a pharmaceutically acceptable salt thereof,

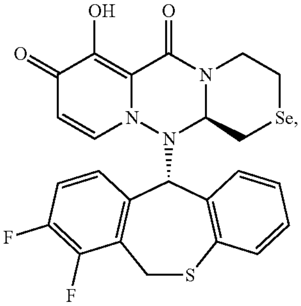
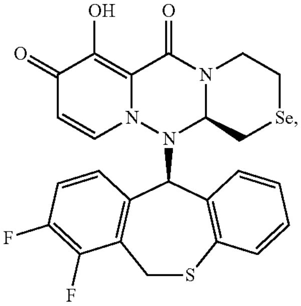
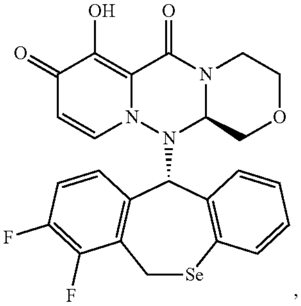
,
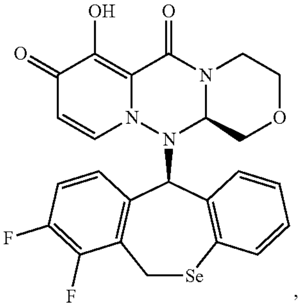
,
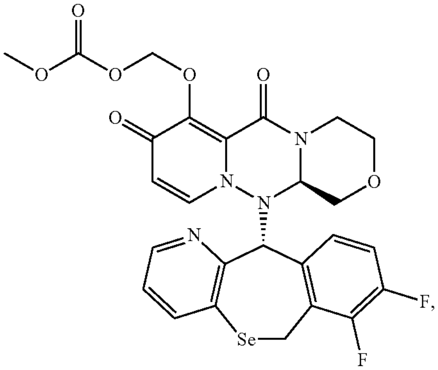
-continued
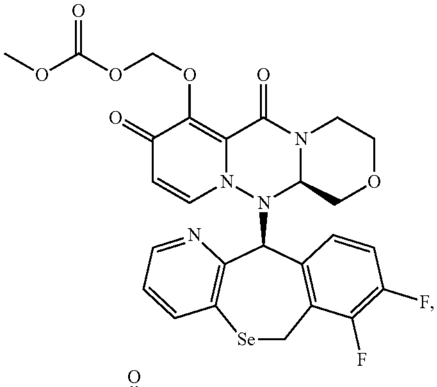
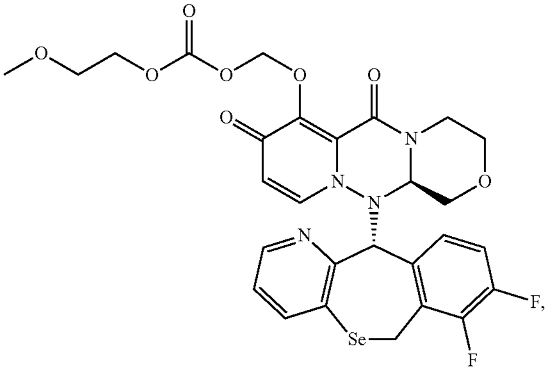
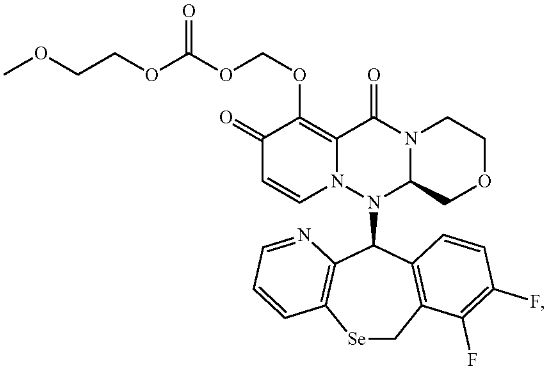
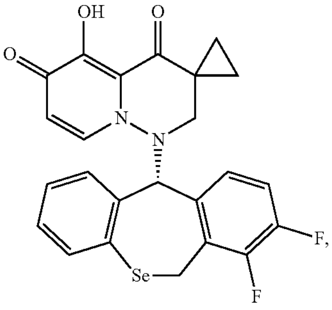
and -continued

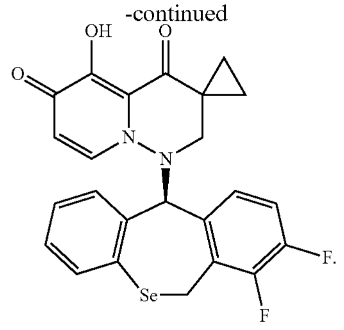

The present disclosure also provides a use of the compound or the pharmaceutically acceptable salt thereof in the manufacture of a medicament for treating diseases related to influenza viruses.

Technical Effect

As an RNA polymerase inhibitor, the compounds of the present disclosure show positive effects in the inhibition assay of influenza virus replication at the cell level. The compounds demonstrate excellent protection against weight loss in animals in an in vivo pharmacodynamic model, with an early recovery period. Test results for the plasma protein binding rate show that the compounds of the present disclosure have a moderate plasma protein binding rate in plasma, and the PK results show that the compounds have good pharmacokinetic properties and good druggability.

RELATED DEFINITIONS

Figure 1:
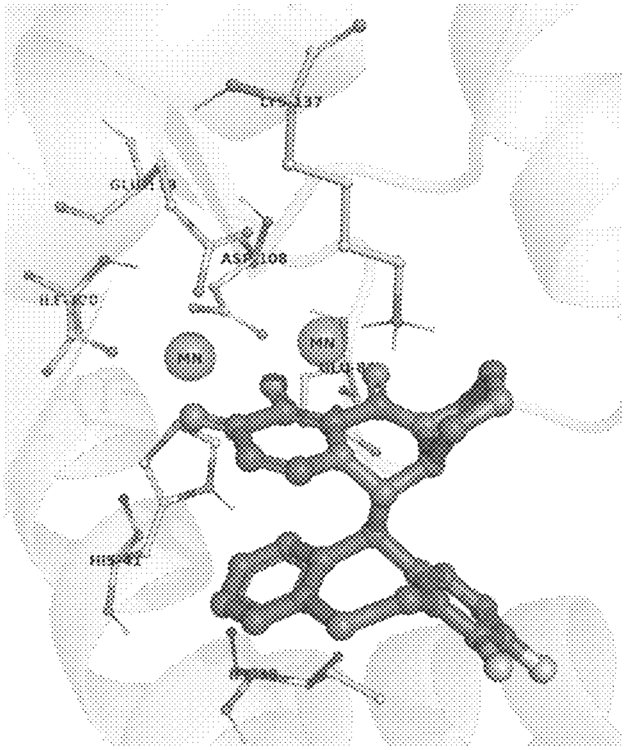
FIG. 1. 3D binding mode of S-033447 with protein (PDB ID: 6FS6).

Unless otherwise specified, the following terms and phrases used herein have the following meanings. A specific term or phrase should not be considered indefinite or unclear in the absence of a particular definition, but should be understood according to the common meaning. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, an allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium, or similar salts. When the compound of the present disclosure contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and salts of an amino acid (such as arginine and the like), and a salt of an organic acid such as glucuronic acid and the like. Certain specific compounds of the present disclosure contain both basic and acidic functional groups, and thus can be converted to any base or acid addition salt.

The pharmaceutically acceptable salt of the present disclosure can be prepared from the parent compound that contains an acidic or basic moiety by a conventional chemical method. Generally, such salt can be prepared by reacting the free acid or base form of the compound with a stoichiometric amount of an appropriate base or acid in water or an organic solvent or a mixture thereof.

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereomers isomers, (D)-isomers, (L)-isomers, and racemic and other mixtures thereof, such as enantiomers or diastereomeric enriched mixtures, all of which are within the scope of the present disclosure. Additional asymmetric carbon atoms may be present in substituents such as alkyl. All these isomers and their mixtures are included within the scope of the present disclosure.

The compound of the present disclosure may contain an unnatural proportion of atomic isotope at one or more than one atom(s) that constitute the compound. For example, the compound can be radiolabeled with a radioactive isotope, such as tritium ($^3H$), iodine-125 ($^{125}I$) or C-14 ($^{14}C$). For another example, deuterated drugs can be formed by replacing hydrogen with heavy hydrogen, the bond formed by deuterium and carbon is stronger than that of ordinary hydrogen and carbon, compared with non-deuterated drugs, deuterated drugs have the advantages of reduced toxic and side effects, increased drug stability, enhanced efficacy, extended biological half-life of drugs, etc. All isotopic variations of the compound of the present disclosure, whether radioactive or not, are encompassed within the scope of the present disclosure.

The term "optional" or "optionally" means that the subsequently described event or circumstance may, but does not necessarily, occur, and the description includes instances where the event or circumstance occurs and instances where it does not.

The term "substituted" means one or more than one hydrogen atom(s) on a specific atom are substituted with the substituent, including deuterium and hydrogen variables, as long as the valence of the specific atom is normal and the substituted compound is stable. When the substituent is an oxygen (i.e., =O), it means two hydrogen atoms are substituted. Positions on an aromatic ring cannot be substituted with a ketone. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as $-(CRR)_0-$, it means that the linking group is a single bond.

When one of the variables is selected from a single bond, it means that the two groups linked by the single bond are connected directly. For example, when L in A-L-Z represents a single bond, the structure of A-L-Z is actually A-Z.

When the enumerative linking group does not indicate the direction for linking, the direction for linking is arbitrary, for example, the linking group L contained in

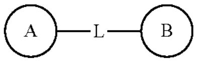

is -M-W-, then -M-W- can link ring A and ring B to form

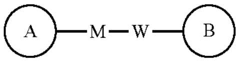

in the direction same as left-to-right reading order, and form

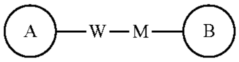

in the direction contrary to left-to-right reading order. A combination of the linking groups, substituents and/or variables thereof is allowed only when such combination can result in a stable compound.

Unless otherwise specified, when a group has one or more linkable sites, any one or more sites of the group can be linked to other groups through chemical bonds. When the linking site of the chemical bond is not positioned, and there is H atom at the linkable site, then the number of H atom at the site will decrease correspondingly with the number of chemical bond linking thereto so as to meet the corresponding valence. The chemical bond between the site and other groups can be represented by a straight solid bond (/),, a straight dashed bond (/) or a wavy line (~).. For example, the straight solid bond in $-OCH_3$ means that it is linked to other groups through the oxygen atom in the group; the straight dashed bond in

means that it is linked to other groups through the two ends of the nitrogen atom in the group; the wave lines in

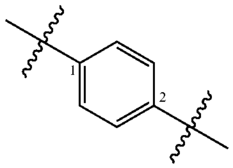 [SMILES: *c1ccc(*)cc1]

means that the phenyl group is linked to other groups through carbon atoms at position 1 and position 2;

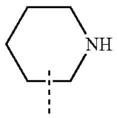

means that it can be linked to other groups through any linkable sites on the piperidinyl by one chemical bond, including at least four types of linkage, including

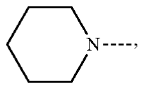,
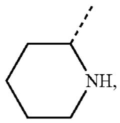,
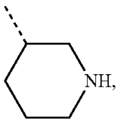,
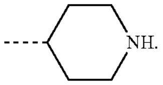.

Even though the H atom is drawn on the —N—,

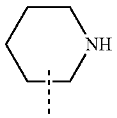

still includes the linkage of

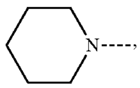, merely when one chemical bond was connected, the H of this site will be reduced by one to the corresponding monovalent piperidinyl.

Unless otherwise specified, the term "$C_{1-3}$ alkyl" refers to a linear or branched saturated hydrocarbon group consisting of 1 to 3 carbon atoms. The $C_{1-3}$ alkyl includes $C_{1-2}$ and $C_{2-3}$ alkyl, etc.; it can be monovalent (such as methyl), divalent (such as methylene), or multivalent (such as methine).

Examples of $C_{1-3}$ alkyl include, but are not limited to, methyl (Me), ethyl (Et), propyl (including n-propyl and isopropyl), etc.

Unless otherwise specified, the term "$C_{1-3}$ alkoxy" refers to an alkyl group containing 1 to 3 carbon atoms that are connected to the rest of the molecule through an oxygen atom. The $C_{1-3}$ alkoxy includes $C_{1-2}$, $C_{2-3}$, $C_3$, and $C_2$ alkoxy, etc. Examples of $C_{1-3}$ alkoxy include, but are not limited to, methoxy, ethoxy, propoxy (including n-propoxy and isopropoxy), etc.

Unless otherwise specified, the term "$C_{1-3}$ alkylamino" refers to an alkyl group containing 1 to 3 carbon atoms that are connected to the rest of the molecule through an amino group. The $C_{1-3}$ alkylamino includes $C_{1-2}$, $C_3$, and $C_2$ akylamino, etc. Examples of $C_{1-3}$ alkylamino include, but are not limited to, $-NHCH_3$, $-N(CH_3)_2$, $-NHCH_2CH_3$, $-N(CH_3)CH_2CH_3$, $-NHCH_2CH_2CH_3$, $-NHCH_2(CH_3)_2$, etc.

Unless otherwise specified, the "$C_{3-5}$ cycloalkyl" refers to a saturated cyclic hydrocarbon group consisting of 3 to 5 carbon atoms, which is a monocyclic system. The $C_{3-5}$ cycloalkyl includes $C_{3-4}$ and $C_{4-5}$ cycloalkyl, etc.; it may be monovalent, divalent, or polyvalent. Examples of $C_{3-5}$ cycloalkyl include, but are not limited to, cyclopropyl, cyclobutyl, cyclopentyl, etc.

Unless otherwise specified, $C_{n-n+m}$ or $C_n$-$C_{n+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, and any range from n to n+m is also included, for example $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$, etc.; similarly, n membered to n+m membered means that the number of atoms on the ring is from n to n+m, for example, 3- to 12-membered ring includes 3-membered ring, 4-membered ring, 5-membered ring, 6-membered ring, 7-membered ring, 8-membered ring, 9-membered ring, 10-membered ring, 11-membered ring, and 12-membered ring, and any range from n to n+m is also included, for example, 3- to 12-membered ring includes 3- to 6-membered ring, 3- to 9-membered ring, 5- to 6-membered ring, 5- to 7-membered ring, 6- to 7-membered ring, 6- to 8-membered ring, and 6- to 10-membered ring, etc.

The term "leaving group" refers to a functional group or atom which can be replaced by another functional group or atom through a substitution reaction (such as affinity substitution reaction). For example, representative leaving groups include triflate; chlorine, bromine, and iodine; sulfonate group, such as mesylate, tosylate, p-bromobenzenesulfonate, p-toluenesulfonates; acyloxy, such as acetoxy, trifluoroacetoxy.

The term "protecting group" includes, but is not limited to, "amino protecting group", "hydroxyl protecting group", or "thio protecting group". The term "amino protecting group" refers to a protecting group suitable for blocking the side reaction on the nitrogen of an amino. Representative amino protecting groups include, but are not limited to: formyl; acyl, such as alkanoyl (e.g., acetyl, trichloroacetyl, or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl, such as benzyl (Bn), trityl (Tr), 1,1-bis-(4'-methoxyphenyl)methyl; silyl, such as trimethylsilyl (TMS) and tert-butyldimethylsilyl (TBS). The term "hydroxyl protecting group" refers to a protecting group suitable for blocking the side reaction on hydroxyl. Representative hydroxy protecting groups include, but are not limited to: alkyl, such as methyl, ethyl, and tert-butyl; acyl, such as alkanoyl (e.g., acetyl); arylmethyl, such as benzyl (Bn), p-methoxybenzyl (PMB), 9-fluorenylmethyl (Fm), and diphenylmethyl (benzhydryl, DPM); silyl, such as trimethylsilyl (TMS) and tert-butyl dimethyl silyl (TBS).

The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred embodiments include but are not limited to the examples of the present disclosure.

The structure of the compounds of the present disclosure can be confirmed by conventional methods known to those skilled in the art, and if the disclosure involves an absolute configuration of a compound, then the absolute configuration can be confirmed by means of conventional techniques in the art. For example, in the case of single crystal X-ray diffraction (SXRD), the absolute configuration can be confirmed by collecting diffraction intensity data from the cultured single crystal using a Bruker D8 venture diffractometer with CuKα radiation as the light source and scanning mode: φ/ω scan, and after collecting the relevant data, the crystal structure can be further analyzed by the direct method (Shelxs97).

The present disclosure uses the following abbreviations: DMAC: N,N-dimethylacetamide, PG: propylene glycol, HP-β-CD: hydroxypropyl-β-cyclodextrin, and Solutol HS-15: macrogol (15)-hydroxystearate.

The solvents used in the present disclosure are commercially available. The compounds of the present disclosure are named according to the conventional naming principles in the art or by ChemDraw® software, and the commercially available compounds use the supplier catalog names.

DETAILED DESCRIPTION OF THE INVENTION

The present disclosure is described in detail by the examples below, but it does not mean that there are any adverse restrictions on the present disclosure. The present disclosure has been described in detail herein, and its specific embodiments have also been disclosed; for one skilled in the art, it is obvious to make various modifications and improvements to the embodiments of the present disclosure without departing from the spirit and scope of the present disclosure.

Reference Example 1

Compound A

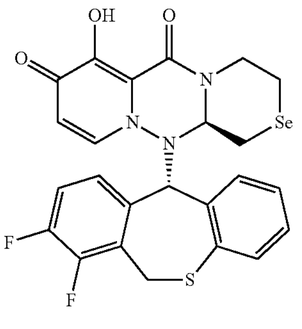

Synthesis Method:
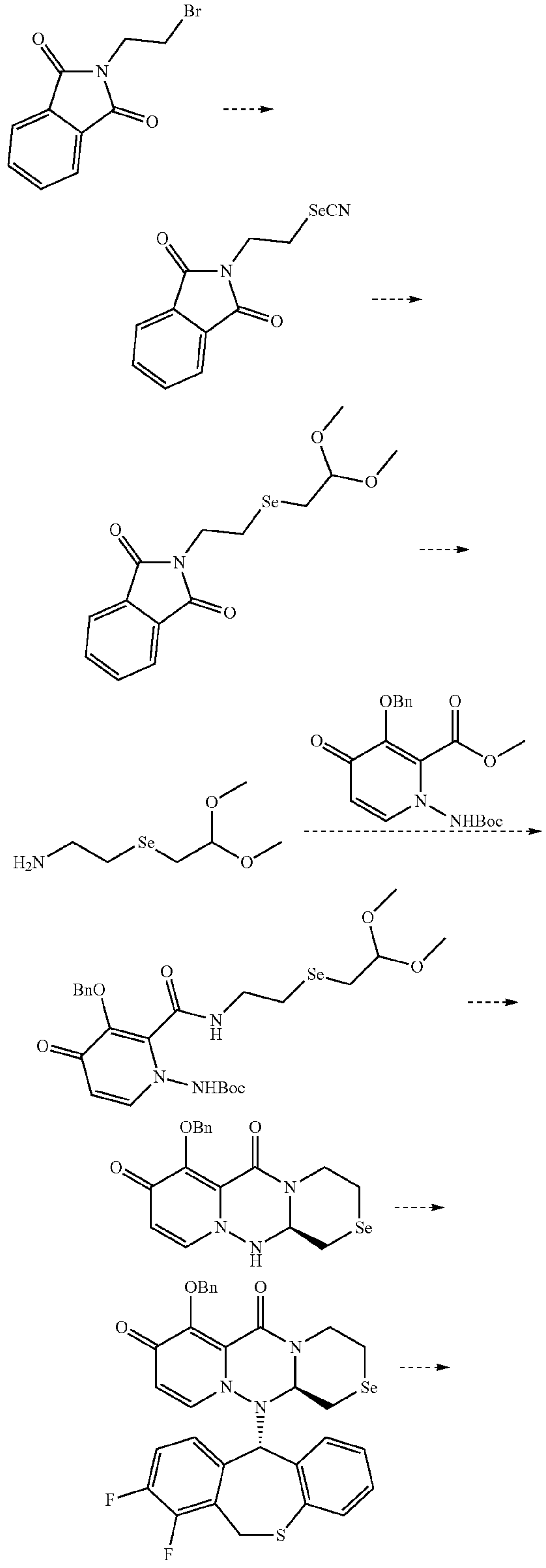
-continued
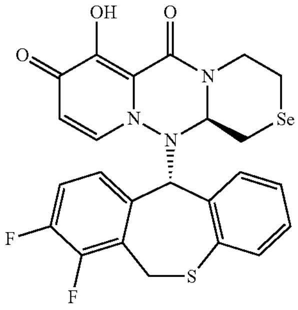
Compound A
Reference Example 2
Compound B
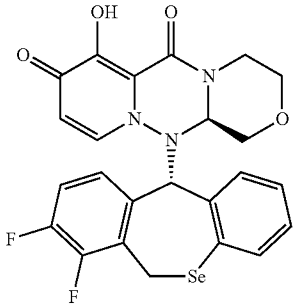
Synthesis Method:
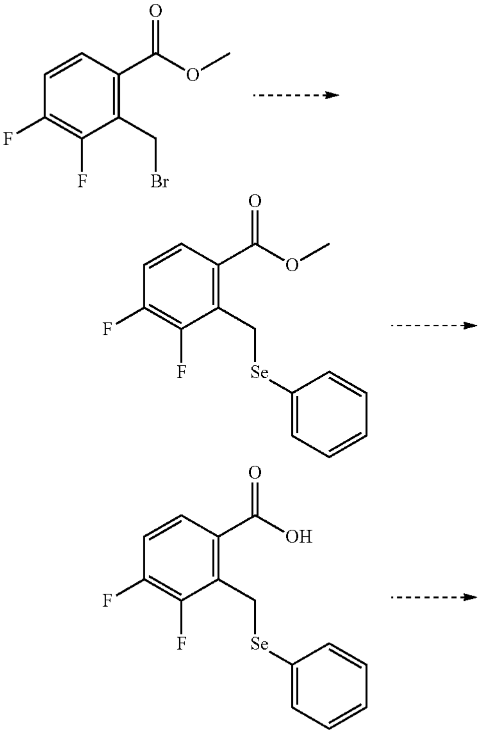

-continued

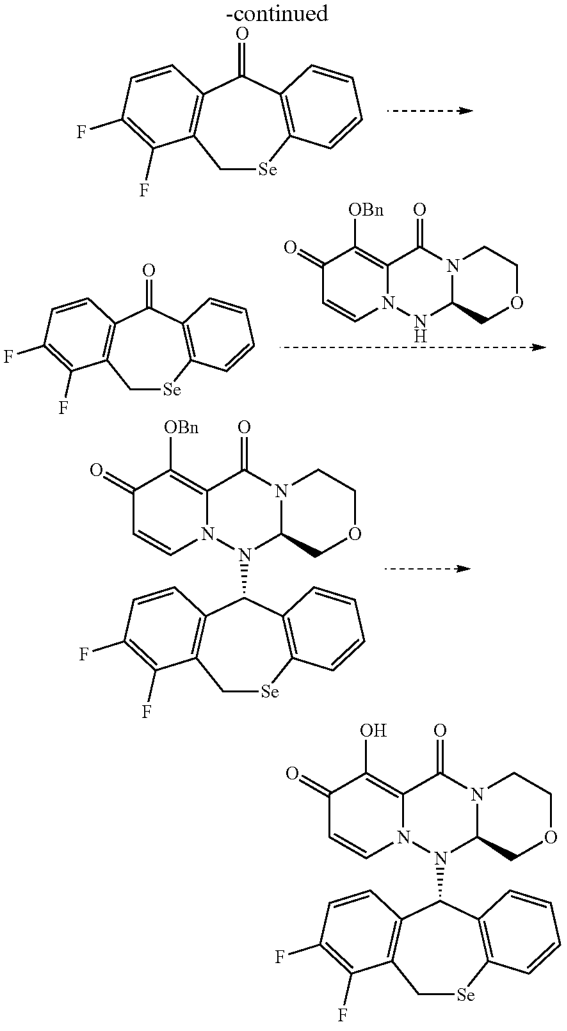

Compound B

Figure 2:
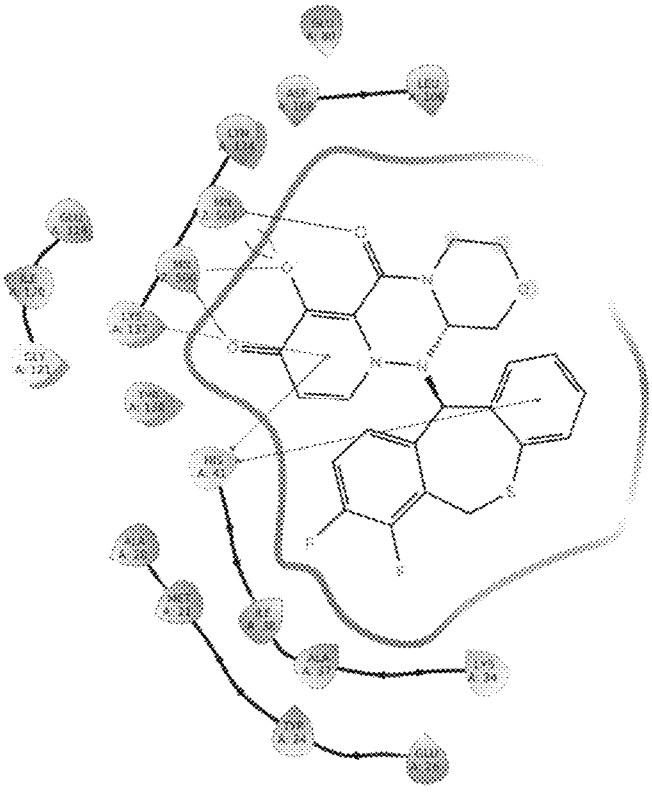
FIG. 2. Illustration of the interactions between S-033447, amino acids, and metal ions.
Figure 3:
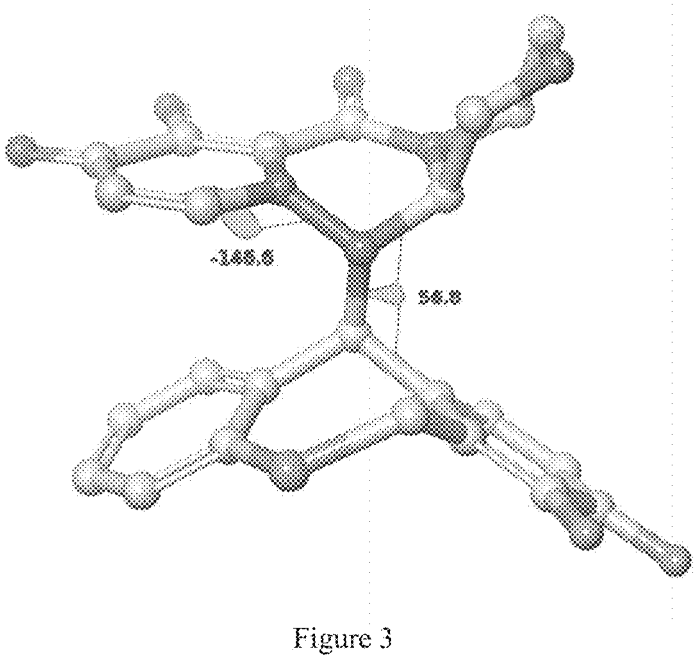
FIG. 3. Two dihedral angles of S-033447 in the low energy conformation.
Figure 4:
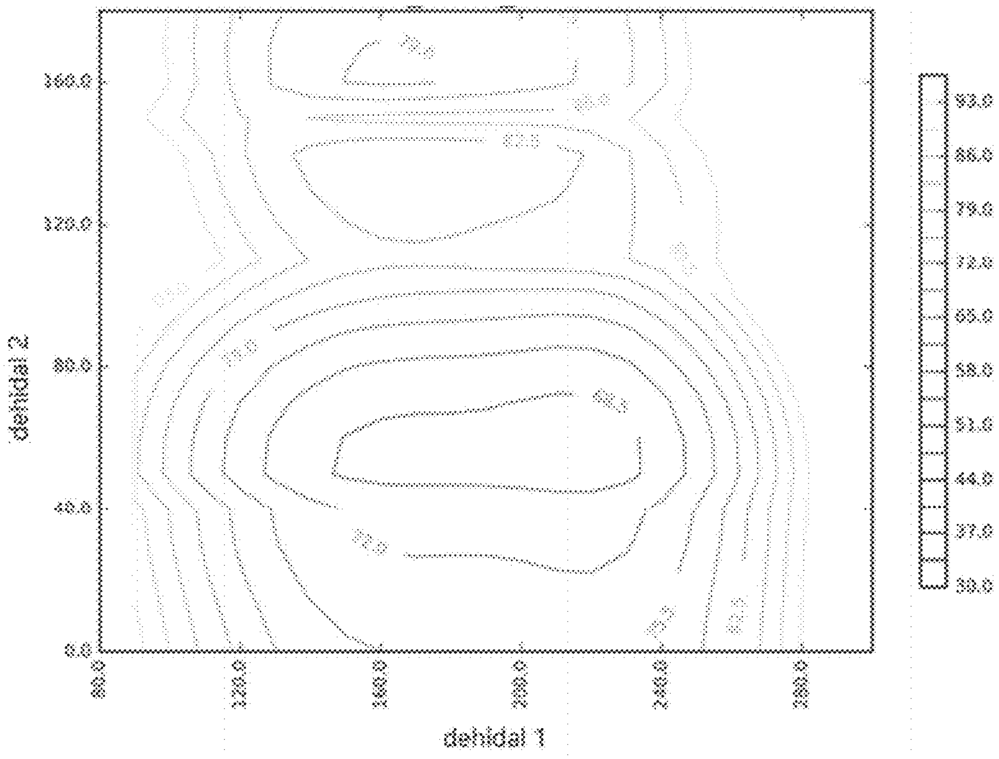
FIG. 4. Energy changes of the two dihedral angles of S-033447 during rotation.

Taking Shionogi & Co.'s anti-influenza drug S-033447 as a reference compound, the low energy conformation of S-033447 was calculated using the Macromodel module of Schrödinger's Maestro software. In its low energy conformation, the dihedral angle (dehidal 1) of the pyridinohexahydropyrimidine (hereafter referred to as the parent nucleus) is −146.6°, and the dihedral angle (dehidal 2) from the parent nucleus to the 2,5-dihydrothiophene is 56.8° (see FIG. 3). The transformation of S-033447 from its low energy conformation to its protein binding mode active conformation (the parent nucleus rotates from −146.6° to −153.7° and the 2,5-dihydrothiophene rotates from 56.8° to 55.0°) requires overcoming an energy barrier of 0.8 kcal/mol (see FIG. 4). The 3D binding mode of 5-033447 and protein (PDB ID: 6FS6) is shown in FIG. 1, and the illustration of the interaction between 5-033447, amino acids, and metal ions is shown in FIG. 2.

Example 1

By observing the binding mode of the active conformation of 5-033447 and 6FS6 protein, we discovered that the benzo 2,5-dihydrothieno difluorobenzyl fragment of 5-033447, while freely rotating, formed the lowest energy barrier conformation (low energy conformation) with the pyridino-hexahydropyrimidine nucleus, which was more consistent with the protein binding mode conformation (active conformation) in the 5-033447 and 6FS6 protein co-crystal. This explained the high binding activity of 5-033447 and 6FS6 protein. In general, the smaller the energy barrier difference between the lowest energy barrier conformation of a small molecule (low energy conformation) and its binding mode conformation in that protein (active conformation), it means that the less energy is lost in the transition from the low energy conformation to the active binding conformation of that protein, and the easier for the compound to bind to the protein and higher binding activity.

To lock the active conformation of 5-033447 and further reduce its rotational barrier, we replaced the O and S of the tetrahydropyran fragment and 2,5-dihydrothiophene fragment of S-033447 with Se through atomic substitution to obtain different cyclopentaselenium and cyclohexaselenium fragments. We also explored the energy barrier difference between the lowest energy barrier conformations of these Se-substituted molecules with the active conformation in the co-crystal of S-033447 and 6FS6 protein.

Figure 5:
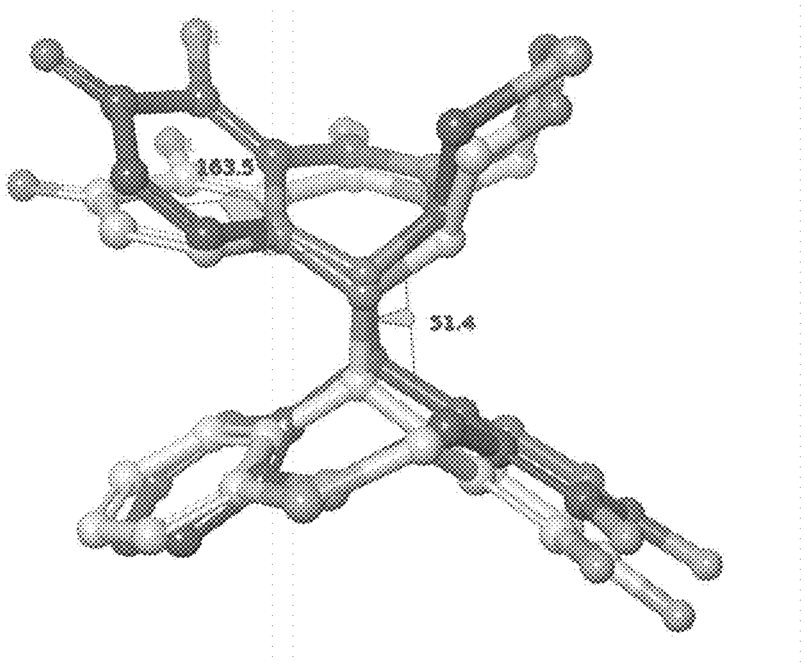
FIG. 5. Comparison of low energy conformations of compound A (dark) and S-033447 (light).
Figure 6:
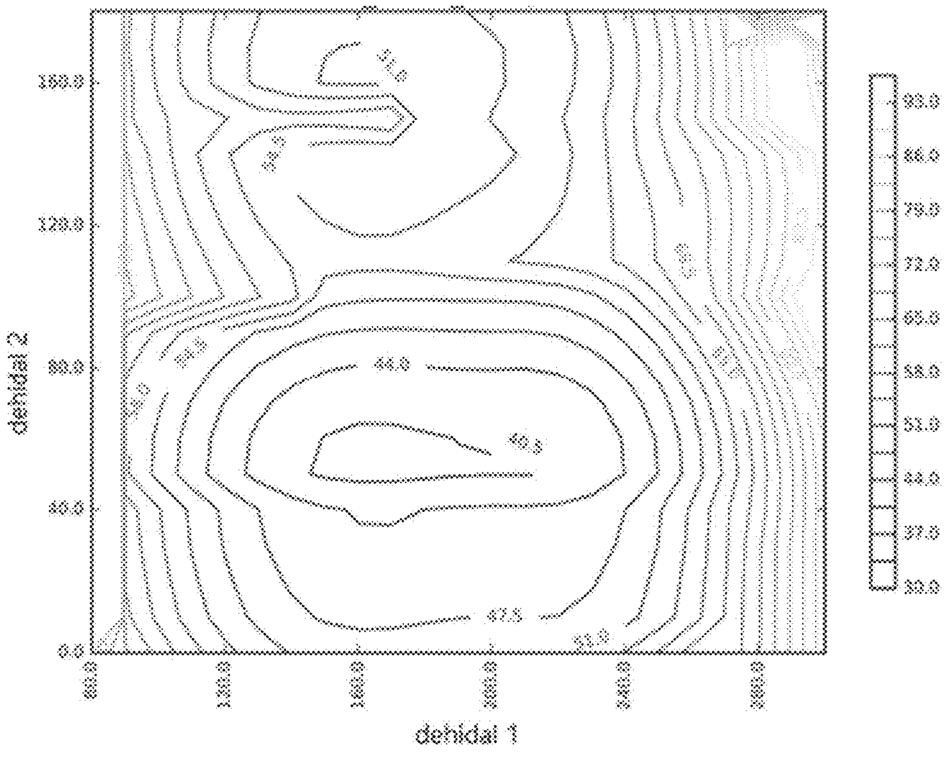
FIG. 6. Energy changes of the two dihedral angles of compound A during rotation.
Figure 7:
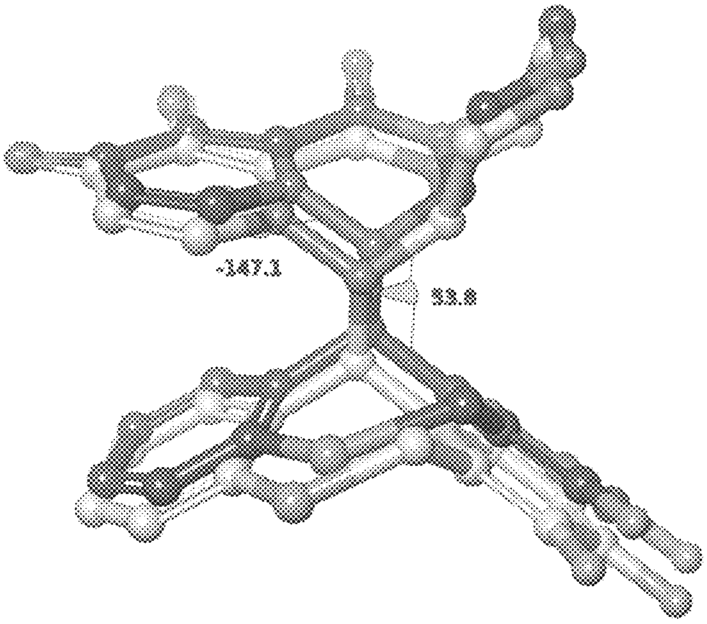
FIG. 7. Comparison of low energy conformations of compound B (dark) and S-033447 (light).
Figure 8:
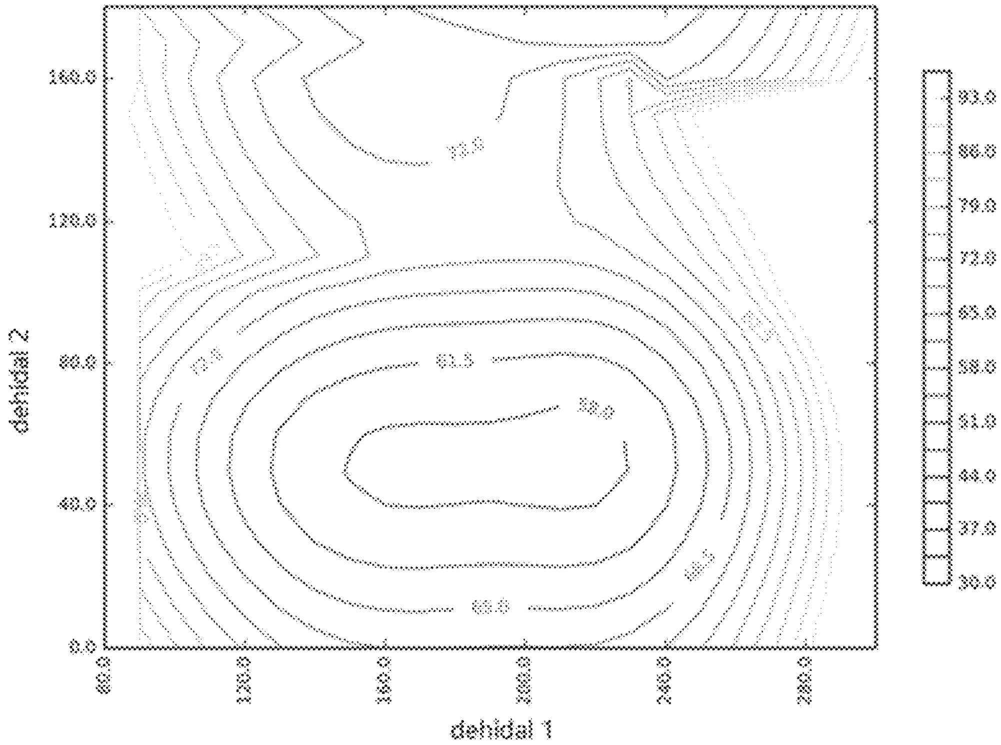
FIG. 8. Energy changes of the two dihedral angles of compound B during rotation.

(1) Rotational dihedral angles and rotational energy barriers of the low energy conformations of compound A and compound B were computed using the Macromodel module, as shown in Table 1. The comparison of the low energy conformations of compound A (dark) and S-033447 (light) is shown in FIG. 5, and the energy changes of the two dihedral angles of compound A during rotation are shown in FIG. 6. Comparison of the low energy conformations of compound B (dark) and S-033447 (light) is shown in FIG. 7, and the energy changes of the two dihedral angles of compound B during rotation are shown in FIG. 8.

TABLE 1

Rotational dihedral angles and rotational energy barriers of the low energy conformations of the compounds of the present disclosure

| Compound | Dihedral 1 (degree) | Dihedral 2 (degree) | E (Kcal/mol) | ΔE (Kcal/mol) |
|---|---|---|---|---|
| S-033447 (active conformation) | −153.7 | 55.0 | 67.6 | 0 |
| S-033447 (low energy conformation) | −146.6 | 56.8 | 66.8 | 0.8 |
| Compound A (low energy conformation) | 163.5 | 51.4 | 39.6 | 28 |
| Compound B (low energy conformation) | −147.1 | 53.8 | 56.8 | 10.8 |

Note:
Dihedral 1 refers to the dihedral angle of pyridino-hexahydropyrimidine; Dihedral 2 refers to the dihedral angle of pyridino-hexahydropyrimidine and 2, 5-dihydrothiophene; ΔE refers to the energy barrier required to transform from the low energy conformation to the active conformation of the protein binding mode of S-033447 (Dihedral 1 is −153.7°, Dihedral 2 is 55.0°).

Conclusion: The low energy conformation of compound B overlaps well with the active conformation of S-033447. The compounds of the present disclosure have a small energy difference between the lowest binding energy barrier in the 6FS6 protein structure and the energy barrier of the reference compound in the active conformation of the protein, making it easier for the compounds of the present disclosure to bind to the protein and potentially exhibit similar or better binding activity than the reference compound in actual binding to the protein.

(2) Rotational dihedral angles of compound B in its low energy conformation were calculated using the Macromodel module, as shown in Table 2.

TABLE 2

| Rotational dihedral angles of the compound of the present disclosure in the low energy conformation | | |
|---|---|---|
| Compound | Dihedral 1 (degree) | Dihedral 2 (degree) |
| Compound B (low energy conformation) | −147.1 | 53.8 |

Note:

Dihedral 1 is the dihedral angle of pyridino-hexahydropyrimidine, and Dihedral 2 is the dihedral angle of pyridino-hexahydropyrimidine and 2, 5-dihydroselenothiophene.

Conclusion: The low energy conformation of compound B is basically consistent with that of S-033447.

Example 2

2 or 2′

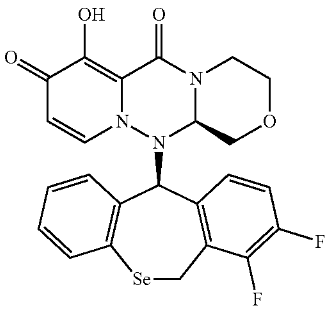

2′ or 2

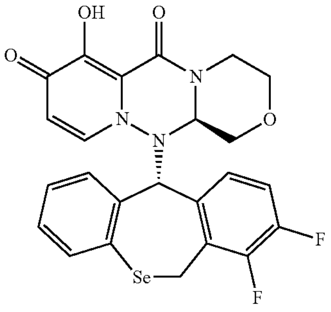

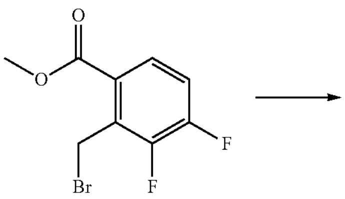

2-1

-continued

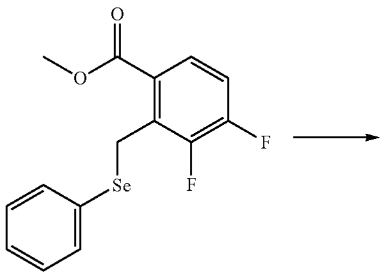

2-2

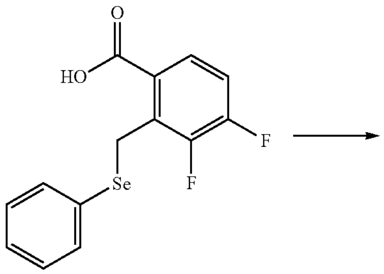

2-3

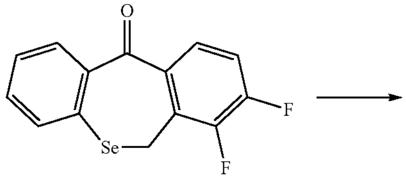

2-4

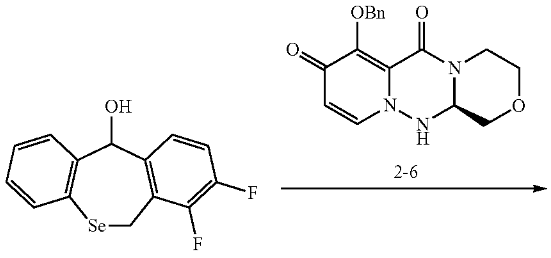

2-6

2-5

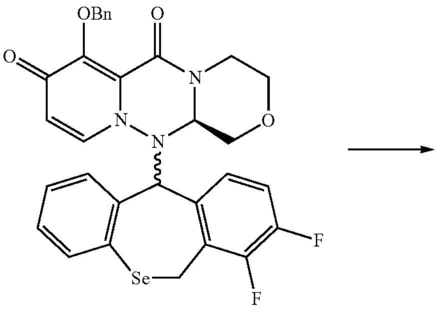

2-7

-continued

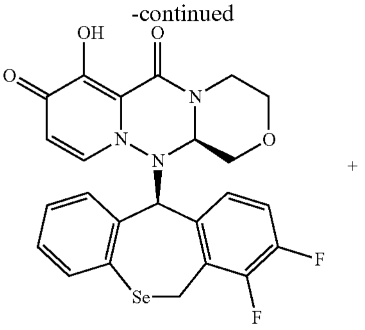

2 or 2'

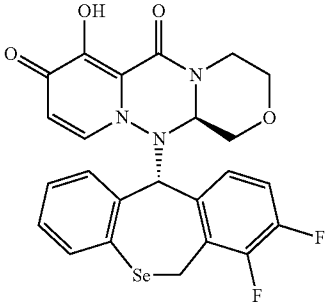

2' or 2

Step 1: Synthesis of Compound 2-2

To water (20 mL) was added sodium dihydrogen phosphate (13.58 g, 113.19 mmol), and added acetonitrile (10 mL) and diphenyl diselenide (1.18 g, 3.77 mmol), then added zinc powder (986.83 mg, 15.09 mmol) in batches. The reaction mixture was stirred at room temperature for 1 hour, then added with compound 2-1 (2 g, 7.55 mmol). The reaction mixture was stirred overnight at room temperature. The reaction mixture was filtered, and the filter cake was washed with ethyl acetate (10 mL×2). The phases were separated. The aqueous phase was extracted with ethyl acetate (10 mL×2). Then the organic phases were combined, washed with saturated brine (20 mL), dried over anhydrous sodium sulfate, filtered, and the filtrate was concentrated to dryness under reduced pressure. The crude product was purified by a silica gel column (petroleum ether:ethyl acetate=1:0 to 10:1) to obtain compound 2-2. MS m/z: 343.0 $[M+H]^+$.

Step 2: Synthesis of Compound 2-3

To methanol (10 mL) and water (5 mL) were added compound 2-2 (1.5 g, 4.40 mmol), and added sodium hydroxide (527.53 mg, 13.19 mmol). The reaction mixture was stirred at 60° C. for 2 hours. The reaction mixture was cooled to room temperature, adjusted to pH=7 with 1 N hydrochloric acid, and extracted with ethyl acetate. The organic phases were combined, washed with saturated brine (10 mL×2), dried over anhydrous sodium sulfate, filtered, and the filtrate was concentrated to dryness under reduced pressure to obtain compound 2-3. The crude product was directly used in the next step.

Step 3: Synthesis of Compound 2-4

To polyphosphoric acid (13 mL) was added compound 2-3 (1.3 g, 3.97 mmol), and the reaction mixture was stirred at 120° C. for 2 hours. The reaction mixture was cooled to 80° C., added to water (50 mL) under stirring. The mixture was stirred for 5 minutes, extracted with dichloromethane (20 mL×2). The organic phases were combined and washed with water (20 mL) and saturated brine (20 mL), dried over anhydrous sodium sulfate, filtered, and the filtrate was concentrated to dryness under reduced pressure. The crude product was purified by a silica gel column (petroleum ether:ethyl acetate=1:0 to 10:1) to obtain compound 2-4. MS m/z: 310.9 $[M+H]^+$.

Step 4: Synthesis of Compound 2-5

To methanol (6 mL) was added compound 2-4 (300 mg, 970.34 μmol), then added sodium borohydride (110.13 mg, 2.91 mmol). The reaction mixture was stirred at room temperature for 1 hour. The reaction mixture was adjusted to pH=7 with 1 N hydrochloric acid and then extracted with dichloromethane (10 mL×2). The organic phases were combined, washed with saturated brine (10 mL), dried over anhydrous sodium sulfate, filtered, and the filtrate was concentrated to dryness under reduced pressure. The crude product was purified by a silica gel column (petroleum ether:ethyl acetate=10:1 to 2:1) to obtain compound 2-5.

Step 5: Synthesis of Compound 2-7

To ethyl acetate (1 mL) was added compound 2-6 (50 mg, 152.75 μmol), and added compound 2-5 (47.53 mg, 152.75 μmol), then added propylphosphonic anhydride (388.82 mg, 611.00 μmol, 363.38 μL, 50% ethyl acetate solution) and methanesulfonic acid (58.72 mg, 611.00 μmol, 43.50 μL), and the reaction mixture was refluxed overnight. The reaction mixture was cooled to room temperature, added with water (10 mL), and extracted with ethyl acetate (5 mL×2). The organic phases were combined and washed with saturated brine (10 mL), dried over anhydrous sodium sulfate, and filtered. The filtrate was concentrated to dryness under reduced pressure. The obtained crude product was purified by a silica gel column (dichloromethane:methanol=1:0 to 10:1) to obtain compound 2-7. MS m/z: 622.0 $[M+H]^+$.

Step 6: Synthesis of Compound 2 and 2'

To N,N-dimethylacetamide (0.5 mL) was added compound 2-7 (10 mg, 16.12 μmol), and added lithium chloride (3.42 mg, 80.58 μmol, 1.65 μL), and the reaction mixture was stirred at 80° C. for 3 hours. The reaction mixture was cooled to room temperature and diluted with acetonitrile (2 mL). The crude reaction mixture was purified by preparative HPLC (column: Xtimate C18 100*30 mm*3 μm; mobile phase: [A: water (0.225% formic acid); B: acetonitrile]; gradient: acetonitrile %: 40%-60%, 8 min) to obtain compound 2 (retention time of 3.205 min) and compound 2' (retention time of 3.301 min).

Compound 2 (retention time of 3.205 min), $^1H$ NMR (400 MHz, deuterated methanol) δ 7.49 (d, J=7.53 Hz, 1H), 7.23-7.32 (m, 2H), 7.16-7.22 (m, 1H), 7.07-7.15 (m, 1H), 6.85-6.97 (m, 2H), 5.85 (d, J=7.28 Hz, 1H), 5.69 (s, 1H), 5.39 (dd, J=2.64, 12.67 Hz, 1H), 4.73 (dd, J=2.89, 10.16 Hz, 1H), 4.62 (br d, J=15.56 Hz, 1H), 4.12 (d, J=12.80 Hz, 1H), 4.07 (dd, J=3.14, 11.17 Hz, 1H), 3.77 (dd, J=3.01, 11.80 Hz, 1H), 3.65 (t, J=10.54 Hz, 1H), 3.43-3.53 (m, 1H), 3.06-3.17 (m, 1H). MS m/z: 532.1 $[M+H]^+$.

Compound 2' (retention time of 3.301 min), $^1H$ NMR (400 MHz, deuterated methanol) δ 7.51 (d, J=7.28 Hz, 1H), 7.35-7.45 (m, 2H), 7.21-7.33 (m, 2H), 6.94-7.04 (m, 1H), 6.82-6.93 (m, 1H), 6.11 (d, J=7.53 Hz, 1H), 5.52-5.68 (m, 2H), 4.42-4.58 (m, 2H), 4.16 (d, J=13.05 Hz, 1H), 4.06 (dd, J=3.14, 10.92 Hz, 1H), 3.60-3.78 (m, 2H), 3.39-3.52 (m, 1H), 2.65-2.81 (m, 1H). MS m/z: 532.1 $[M+H]^+$.

Example 3
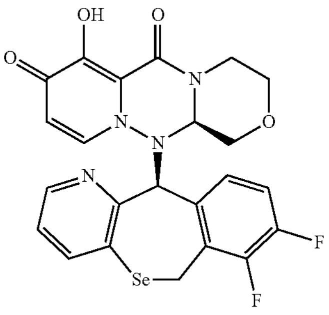
3 or 3′
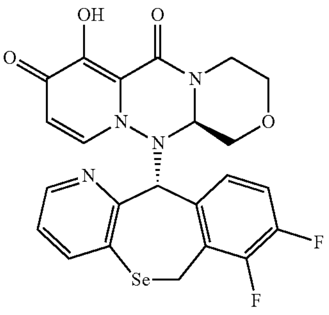
3′ or 3
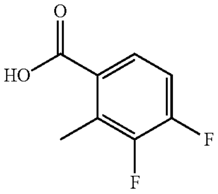
3-1
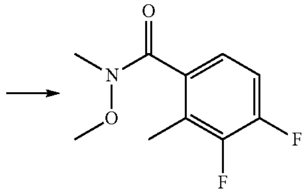
3-2
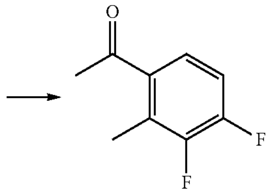
3-3
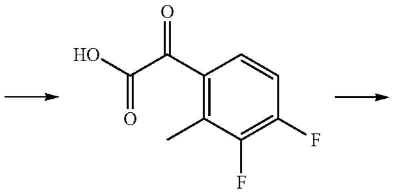
3-4
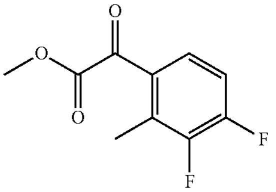
3-5
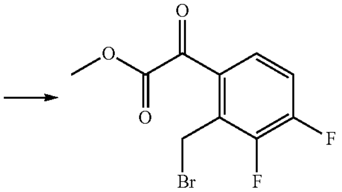
3-6
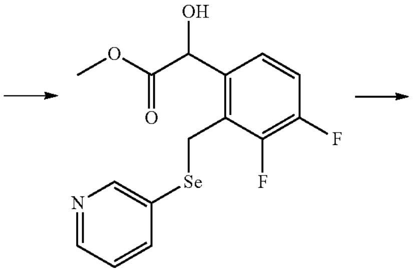
3-7
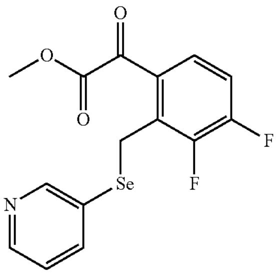
3-8
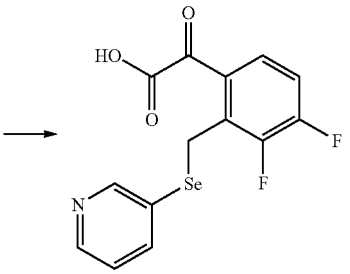
3-9
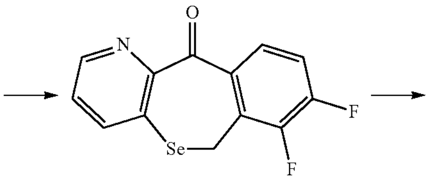
3-10
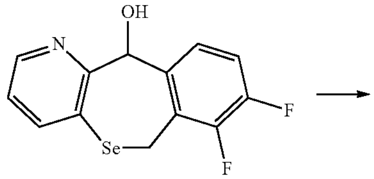
3-11

-continued

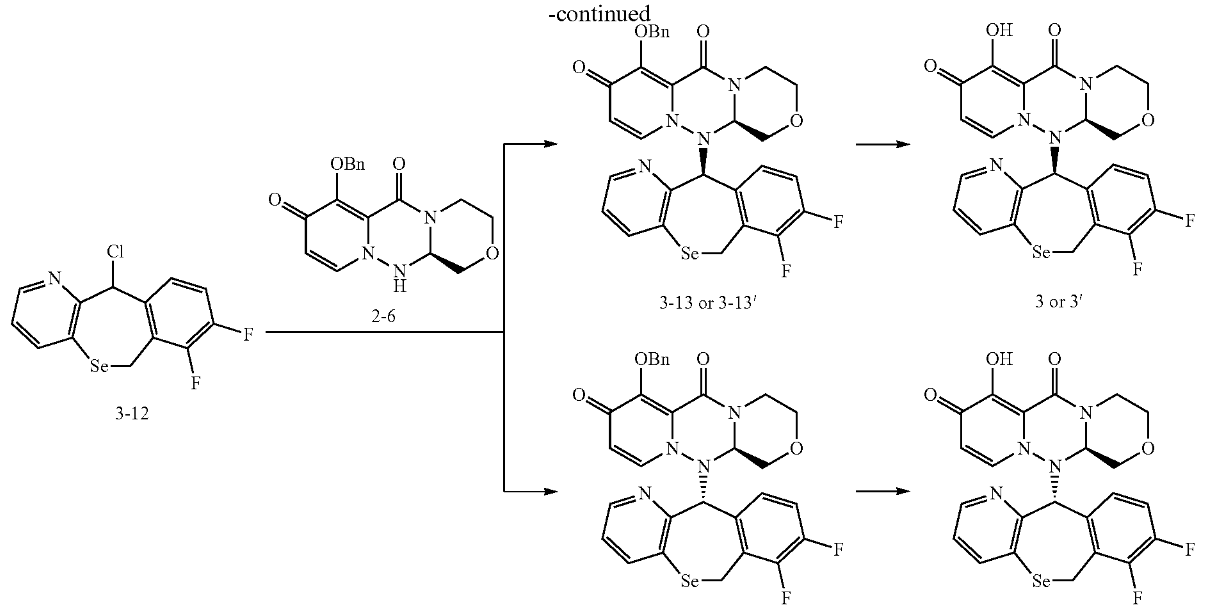

3-12

2-6

3-13 or 3-13′

3 or 3′

3-13′ or 3-13

3′ or 3

Step 1: Synthesis of Compound 3-2

Compound 3-1 (66 g, 383.43 mmol) was dissolved in dichloromethane (460 mL) and N,N-dimethylformamide (280.27 mg, 3.83 mmol, 295.02 μL) was added thereto. Oxalyl chloride (73.00 g, 575.15 mmol, 50.35 mL) was added dropwise to the reaction mixture. After the addition, the reaction mixture was stirred at 20° C. for 30 minutes and then concentrated to dryness under reduced pressure. To the crude product was added dichloromethane (460 mL), and added triethylamine (77.60 g, 766.87 mmol, 106.74 mL) and N,O-dimethylhydroxylamine hydrochloride (37.40 g, 383.43 mmol) with stirring, and the reaction mixture was stirred at 20° C. for 1 hour. The reaction mixture was added with water (100 mL) and the phases were separated. The aqueous phase was extracted with dichloromethane (50 mL×2). The organic phases were combined, washed with dilute hydrochloric acid (0.2 M, 50 mL), saturated sodium bicarbonate aqueous solution (50 mL), and saturated brine (50 mL) respectively, dried over anhydrous sodium sulfate, filtered, and the filtrate was concentrated to dryness under reduced pressure to obtain compound 3-2. $^1$H NMR (400 MHz, deuterated chloroform) δ 7.02-7.05 (m, 2H), 3.81 (brs, 3H), 3.49 (s, 3H), 2.28 (s, 3H).

Step 2: Synthesis of Compound 3-3

Compound 3-2 (20 g, 92.94 mmol) was dissolved in tetrahydrofuran (200 mL), and methylmagnesium bromide (3 M, 37.18 mL) was added dropwise thereto at 0° C. After the addition, the reaction mixture was warmed to 20° C. and stirred for 2 hours. The reaction mixture was quenched with 1 M hydrochloric acid, adjusted to pH=7, and extracted with ethyl acetate (100 mL×2). The organic phases were combined, washed with dilute hydrochloric acid (0.2 M, 50 mL), saturated sodium bicarbonate solution (50 mL), and saturated brine (50 mL) respectively, dried over anhydrous sodium sulfate, filtered, and the filtrate was concentrated to dryness under reduced pressure to obtain compound 3-3. $^1$H NMR (400 MHz, deuterated chloroform) δ 7.47-7.50 (m, 1H), 7.03-7.07 (m, 1H), 2.60 (s, 3H), 2.47 (s, 3H).

Step 3: Synthesis of Compound 3-4

Compound 3-3 (15 g, 88.15 mmol) was dissolved in pyridine (90 mL). Selenium dioxide (19.56 g, 176.31 mmol) was then added thereto, and the reaction mixture was stirred at 110° C. for 12 hours. The reaction mixture was cooled to room temperature, filtered, and the filtrate was concentrated to dryness under reduced pressure. The crude product was added with water (50 mL) and the pH of the mixture was adjusted to 4 with 1 M hydrochloric acid. The mixture was extracted with ethyl acetate (50 mL×3). The organic phases were combined and washed with saturated brine (50 mL), dried over anhydrous sodium sulfate, and filtered. The filtrate was concentrated to dryness under reduced pressure to obtain compound 3-4. $^1$H NMR (400 MHz, deuterated methanol) δ 7.64-7.68 (m, 1H), 7.30-7.32 (m, 1H), 2.52 (s, 3H).

Step 4: Synthesis of Compound 3-5

Compound 3-4 (15 g, 74.95 mmol) was dissolved in dichloromethane (60 mL) and methanol (60 mL). Trimethylsilyldiazomethane (2 M, 44.97 mL) was added dropwise at a controlled temperature between 0 to 20° C. The reaction mixture was stirred at 20° C. for 2 hours. Then, acetic acid (3 mL) was added thereto and the reaction mixture was stirred for 5 minutes. The reaction mixture was concentrated to dryness under reduced pressure. Then, water (50 mL) was added thereto, and the mixture was extracted with dichloromethane (50 mL×2). The organic phases were combined and washed with saturated brine (30 mL), dried over anhydrous sodium sulfate, and filtered. The filtrate was concentrated to dryness under reduced pressure. The obtained crude product was purified by a silica gel column (ethyl acetate/petroleum ether, ratio of ethyl acetate: 0 to 20%) to obtain compound 3-5. $^1$H NMR (400 MHz, deuterated chloroform) δ 7.51-7.55 (m, 1H), 7.12-7.16 (m, 1H), 3.98 (s, 3H), 2.54 (s, 3H).

Step 5: Synthesis of Compound 3-6

Compound 3-5 (5 g, 23.35 mmol) was dissolved in 1,2-dichloroethane (50 mL), and added with N-bromosuccinimide (8.31 g, 46.69 mmol) and azobisisobutyronitrile (383.37 mg, 2.33 mmol). The reaction mixture was stirred at 80° C. for 12 hours. The reaction mixture was cooled to room temperature, sequentially washed with saturated sodium sulfite solution (20 mL), water (20 mL), and saturated brine (20 mL), dried over anhydrous sodium sulfate, filtered, and the filtrate was concentrated to dryness under reduced pressure. The obtained crude product was purified by a silica gel column (ethyl acetate/petroleum ether, ratio of ethyl acetate: 0 to 5%) to obtain compound 3-6. $^1$H NMR (400 MHz, deuterated chloroform) δ 7.61-7.64 (m, 1H), 7.26-7.31 (m, 1H), 4.94 (s, 2H), 3.99 (s, 3H).

Step 6: Synthesis of Compound 3-7

Sodium dihydrogen phosphate (11.52 g, 96.05 mmol) was dissolved in water (60 mL), sequentially added with acetonitrile (30 mL) and 1,2-di(pyridin-3-yl)diselane (3.62 g, 11.53 mmol), then added with zinc powder (1.88 g, 28.82 mmol) in batches, and the reaction mixture was stirred at 20° C. for 30 minutes. Compound 3-6 (5.63 g, 19.21 mmol) was added thereto, and the reaction mixture was stirred at 20° C. for 3 hours. The reaction mixture was filtered, and the filtrate was extracted with ethyl acetate (30 mL×2). The organic phases were combined, washed with saturated brine (30 mL), dried over anhydrous sodium sulfate, and filtered. The filtrate was concentrated to dryness under reduced pressure. The obtained crude product was purified by a silica gel column (ethyl acetate/petroleum ether, ratio of ethyl acetate: 0 to 60%) to obtain compound 3-7. MS(ESI) m/z: 373.8 [M+H]$^+$.

Step 7: Synthesis of Compound 3-8

Compound 3-7 (4.2 g, 11.28 mmol) was dissolved in dichloromethane (80 mL), and added with Dess-Martin periodinane (7.18 g, 16.93 mmol), and the reaction mixture at 20° C. for 12 hours. Saturated sodium sulfite solution (30 mL) was added to the reaction mixture, and the reaction mixture was stirred for 5 minutes. The reaction mixture was extracted with dichloromethane (30 mL×2). Then the organic phases were combined, washed with saturated brine (30 mL), dried over anhydrous sodium sulfate, filtered, and the filtrate was concentrated to dryness under reduced pressure. The obtained crude product was purified by a silica gel column (ethyl acetate/petroleum ether, ratio of ethyl acetate: 0 to 50%) to obtain compound 3-8. MS(ESI) m/z: 371.9 [M+H]$^+$.

Step 8: Synthesis of Compound 3-9

Compound 3-8 (2.9 g, 7.83 mmol) was dissolved in tetrahydrofuran (16 mL). Sodium hydroxide aqueous solution (626.67 mg, 15.67 mmol, 4 mL) was then added thereto, and the reaction mixture was stirred at 20° C. for 1 hour. The reaction mixture was concentrated under reduced pressure to remove most of the tetrahydrofuran. The aqueous phase was adjusted to pH=6 with 1 N hydrochloric acid, then filtered. The filter cake was dried under reduced pressure to obtain compound 3-9. MS(ESI) m/z: 357.9 [M+H]$^+$.

Step 9: Synthesis of Compound 3-10

Compound 3-9 (2.3 g, 6.46 mmol) was dissolved in dimethyl sulfoxide (23 mL), sequentially added with ammonium persulfate (2.95 g, 12.91 mmol), silver nitrate (109.69 mg, 645.74 μmol), and concentrated sulfuric acid (633.34 mg, 6.46 mmol). The reaction mixture was stirred at 50° C. for 3 hours. The reaction mixture was added with saturated sodium bicarbonate aqueous solution (20 mL), water (10 mL), and dichloromethane (20 mL) respectively, and stirred for 5 minutes and then filtered. The phases in the filtrate were separated and the aqueous phase was extracted with dichloromethane (10 mL). The organic phases were combined, washed with saturated brine (30 mL×3), dried over anhydrous sodium sulfate, and filtered. The filtrate was concentrated to dryness under reduced pressure. The obtained crude product was purified by a silica gel column (ethyl acetate/petroleum ether, ratio of ethyl acetate: 0 to 50%) to obtain compound 3-10. MS(ESI) m/z: 311.8 [M+H]$^+$.

Step 10: Synthesis of Compound 3-11

Compound 3-10 (390 mg, 1.26 mmol) was dissolved in isopropanol (8 mL), added with sodium borohydride (95.14 mg, 2.51 mmol), and the reaction mixture was stirred at 20° C. for 1 hour. The pH of the reaction mixture was adjusted to pH=7 with 1 N hydrochloric acid, and the mixture was extracted with ethyl acetate (15 mL×2). The organic phases were combined, washed with saturated brine (10 mL), dried over anhydrous sodium sulfate, and filtered. The filtrate was concentrated to dryness under reduced pressure. The obtained crude product was purified by a silica gel column (ethyl acetate/petroleum ether, ratio of ethyl acetate: 0 to 50%) to obtain compound 3-11. MS(ESI) m/z: 313.8 [M+H]$^+$.

Step 11: Synthesis of Compound 3-12

Compound 3-11 (330 mg, 1.06 mmol) was dissolved in dichloromethane (6 mL), added with thionyl chloride (251.53 mg, 2.11 mmol, 153.37 μL), and the reaction mixture was stirred at 20° C. for 1 hour. The reaction mixture was concentrated to dryness under reduced pressure to obtain compound 3-12. The crude product was directly used in the next reaction step.

Step 12: Synthesis of Compounds 3-13 and 3-13'

Compound 2-6 (340 mg, 1.04 mmol) was dissolved in acetonitrile (6 mL), added with compound 3-12 (343.41 mg, 1.04 mmol) and cesium carbonate (676.86 mg, 2.08 mmol), and the reaction mixture was stirred at 60° C. for 12 hours. The reaction mixture was cooled to room temperature, added with water (5 mL), extracted with ethyl acetate (5 mL×3). The organic phases were combined, washed with saturated brine (5 mL), dried over anhydrous sodium sulfate, and filtered. The filtrate was concentrated to dryness under reduced pressure. The obtained crude product was purified by a silica gel column (methanol/dichloromethane, ratio of methanol: 0 to 5%), and the obtained compound was detected by supercritical fluid chromatography (analysis method: column type: Chiralpak AD-3 (50 mm*4.6 mm, 3 μm); mobile phase: [A: carbon dioxide, B: 0.05% diethylamine/ethanol]; gradient: the concentration of mobile phase B increased from 5% to 40% within 2 minutes, maintained at 40% for 1.2 minutes, then maintained at 5% for 0.8 minutes). The purified product was analyzed to be a mixture. The chiral isomers of compound 3-13 (retention time of 1.831 min, ee=96.1%) and compound 3-13' (retention time of 2.031 min, ee=100%) were separated through chiral separation (column type: DAICEL CHIRALPAK AD (250 mm*30 mm, 10 μm); mobile phase: [A: carbon dioxide, B: 0.1% ammonia water/ethanol]; gradient: the concentration of mobile phase B was kept at 40%).

Step 13: Synthesis of Compound 3

To N,N-dimethylacetamide (1 mL) was added compound 3-13 (6 mg, 9.65 μmol), added lithium chloride (2.05 mg, 48.27 μmol), and the reaction mixture was stirred at 80° C. for 12 hours. The reaction mixture was cooled to room temperature and diluted with acetonitrile (1 mL). The crude reaction mixture was purified by preparative HPLC (column: Phenomenex Gemini-NX C18 75*30 mm*3 μm; mobile phase: [A: water (0.225% formic acid); B: acetonitrile]; gradient: acetonitrile %: 30% to 53%, 5 minutes) to obtain compound 3. $^1$H NMR (400 MHz, deuterated methanol) δ 7.98-8.09 (m, 1H), 7.70 (dd, J=1.51, 8.03 Hz, 1H), 7.41 (d, J=7.53 Hz, 1H), 7.18-7.31 (m, 2H), 7.13 (dd, J=4.52, 8.03 Hz, 1H), 5.75-5.88 (m, 2H), 5.40-5.53 (m, 1H), 4.71 (dd, J=3.01, 10.04 Hz, 1H), 4.63 (br s, 1H), 4.17 (d, J=12.55 Hz, 1H), 4.07 (dd, J=3.01, 11.04 Hz, 1H), 3.77 (dd, J=3.01, 11.54 Hz, 1H), 3.66 (t, J=10.54 Hz, 1H), 3.48 (dt, J=2.51, 11.80 Hz, 1H), 3.04-3.18 (m, 1H). MS(ESI) m/z: 533.1 [M+H]$^+$.

Step 14: Synthesis of Compound 3'

To N,N-dimethylacetamide (1 mL) was added compound 3-13' (5 mg, 8.05 μmol), added lithium chloride (1.71 mg, 40.23 μmol), and the reaction mixture was stirred at 80° C. for 12 hours. The reaction mixture was cooled to room temperature and diluted with acetonitrile (1 mL). The crude reaction mixture was purified by preparative HPLC (column: Phenomenex Gemini-NX C18 75*30 mm*3 μm; mobile phase: [A: water (0.225% formic acid); B: acetonitrile]; gradient: acetonitrile %: 30%-53%, 5 minutes) to obtain compound 3'. $^1$H NMR (400 MHz, deuterated methanol) δ 8.39-8.49 (m, 1H), 7.83 (dd, J=1.51, 8.03 Hz, 1H), 7.26-7.39 (m, 2H), 6.95-7.10 (m, 1H), 6.85 (br s, 1H), 5.92 (d, J=7.53 Hz, 1H), 5.72 (s, 1H), 5.64 (br d, J=13.55 Hz, 1H), 4.50-4.58 (m, 1H), 4.36 (br d, J=7.53 Hz, 1H), 4.16-4.24 (m, 1H), 4.05 (dd, J=3.01, 11.04 Hz, 1H), 3.74 (dd, J=3.51, 11.54 Hz, 1H), 3.65 (t, J=10.54 Hz, 1H), 3.47 (dt, J=2.51, 11.80 Hz, 1H), 2.79-2.91 (m, 1H). MS(ESI) m/z: 533.1 [M+H]$^+$.

Example 4

4

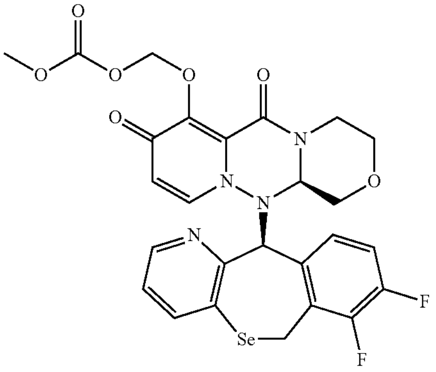

or

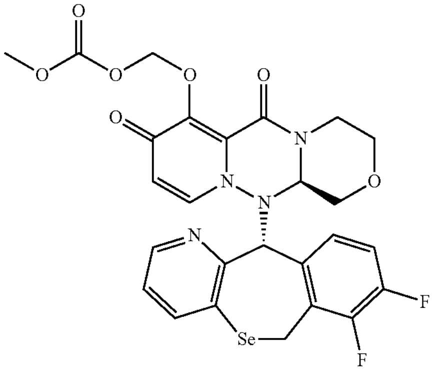

-continued

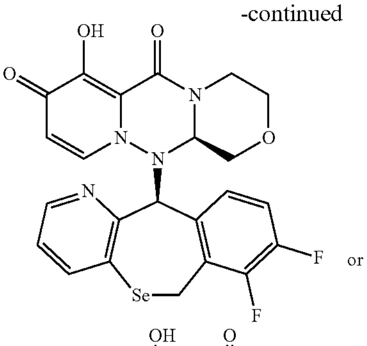

or

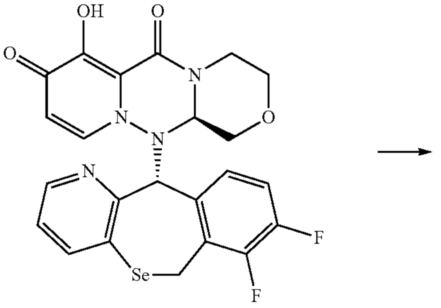

3

4

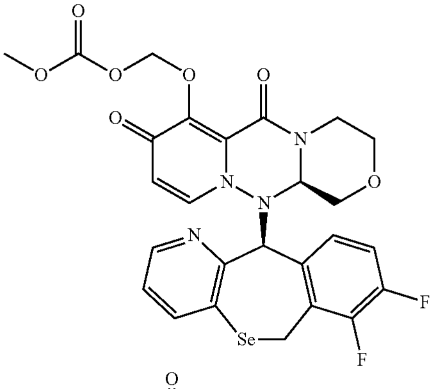

or

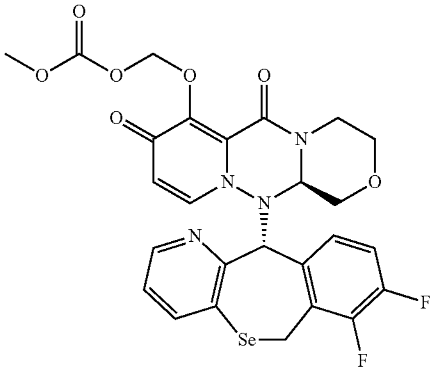

To N,N-dimethylacetamide (2 mL) was added compound 3 (130.00 mg, 244.65 μmol), sequentially added chloromethyl methyl carbonate (45.70 mg, 366.98 μmol), potassium carbonate (67.63 mg, 489.30 μmol), and potassium iodide (40.61 mg, 244.65 μmol), and the reaction mixture was stirred at 70° C. for 3 hours. The reaction mixture was cooled to room temperature, added with water (10 mL), and extracted with ethyl acetate (10 mL×2). The organic phase was washed with saturated brine (10 mL×4), dried over anhydrous sodium sulfate, and filtered. The filtrate was concentrated to dryness under reduced pressure. The obtained crude product was purified by a silica gel column (dichloromethane:methanol=1:0 to 20:1) to obtain compound 4. $^1$H NMR (400 MHz, deuterated chloroform) δ 8.03 (dd, J=1.00, 4.52 Hz, 1H), 7.44 (dd, J=1.51, 8.03 Hz, 1H), 6.99-7.16 (m, 3H), 6.95 (dd, J=4.52, 8.03 Hz, 1H), 5.90 (d, J=6.53 Hz, 1H), 5.74-5.85 (m, 1H), 5.22-5.35 (m, 3H), 4.60 (dd, J=2.01, 13.55 Hz, 1H), 4.50 (dd, J=3.01, 10.04 Hz, 1H), 4.03 (d, J=12.55 Hz, 1H), 3.95 (dd, J=3.01, 11.04 Hz, 1H), 3.77-3.83 (m, 3H), 3.73 (dd, J=3.01, 12.05 Hz, 1H), 3.54 (t, J=10.54 Hz, 1H), 3.41 (dt, J=2.51, 11.80 Hz, 1H), 2.85-2.97 (m, 1H); MS(ESI) m/z: 621.0 [M+H]$^+$.

The absolute configuration of compound 4 was confirmed by single crystal X-ray diffraction (SXRD):

4

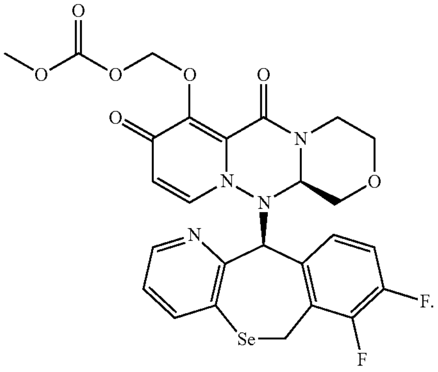

Example 5

5

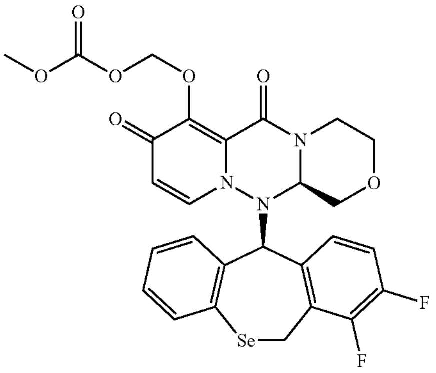

or

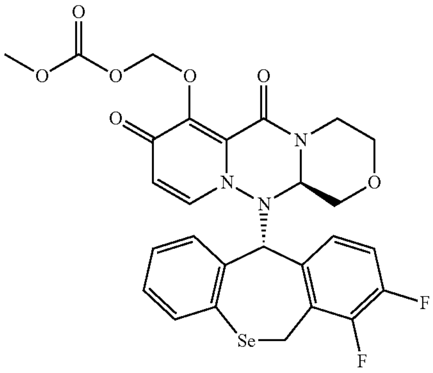

-continued

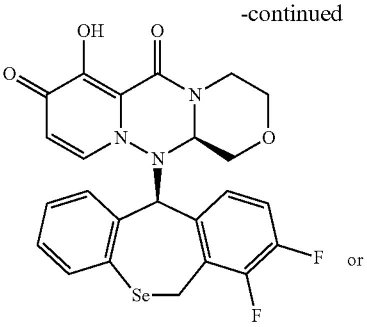

or

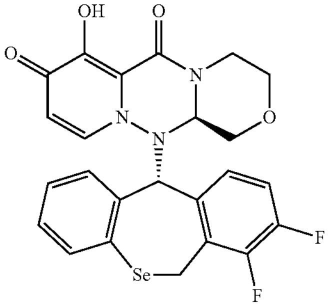

2

5

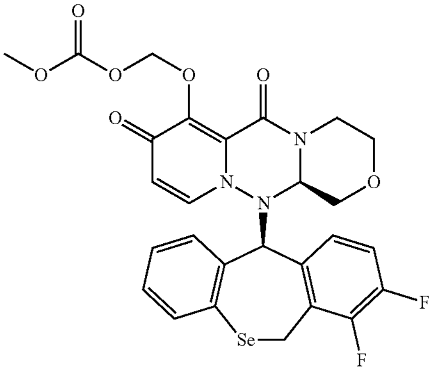

or

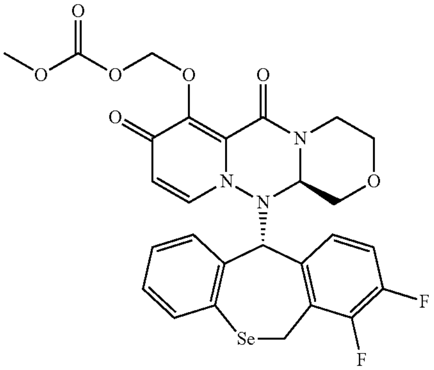

To N,N-dimethylacetamide (1 mL) was added compound 2 (30.00 mg, 56.56 μmol), sequentially added chloromethyl methyl carbonate (14.09 mg, 113.13 μmol), potassium carbonate (15.64 mg, 113.13 μmol), and potassium iodide (9.39 mg, 56.56 μmol), and the reaction mixture was stirred at 70° C. for 3 hours. The reaction mixture was cooled to room temperature, added with water (3 mL), and extracted with ethyl acetate (3 mL×2). The organic phase was washed with saturated brine (3 mL×3), dried over anhydrous sodium sulfate, and filtered. The filtrate was concentrated to dryness under reduced pressure. The obtained crude product was purified by a preparative thin-layer silica gel plate (dichloromethane:methanol=10:1) to obtain compound 5. $^1$H NMR (400 MHz, deuterated methanol) δ 7.54 (d, J=7.53 Hz, 1H), 7.13-7.28 (m, 3H), 7.07-7.13 (m, 1H), 6.99-7.05 (m, 1H), 6.90-6.97 (m, 1H), 5.92 (d, J=7.78 Hz, 1H), 5.75-5.83 (m, 2H), 5.66 (s, 1H), 5.39 (dd, J=2.64, 12.67 Hz, 1H), 4.65 (dd, J=3.01, 10.04 Hz, 1H), 4.55 (dd, J=2.13, 13.43 Hz, 1H), 4.03-4.15 (m, 2H), 3.80-3.85 (m, 3H), 3.75 (dd, J=3.26, 11.54 Hz, 1H), 3.56 (t, J=10.54 Hz, 1H), 3.42 (dt, J=2.51, 11.67 Hz, 1H), 2.98-3.08 (m, 1H); MS(ESI) m/z: 620.1 [M+H]$^+$.
Example 6
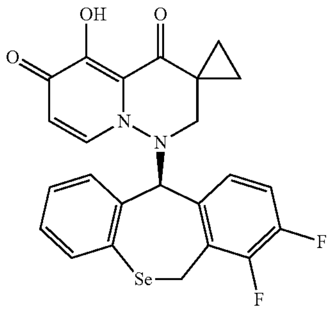
6 or 6′
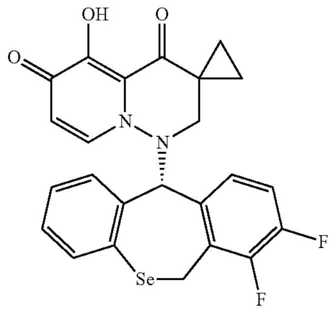
6′ or 6
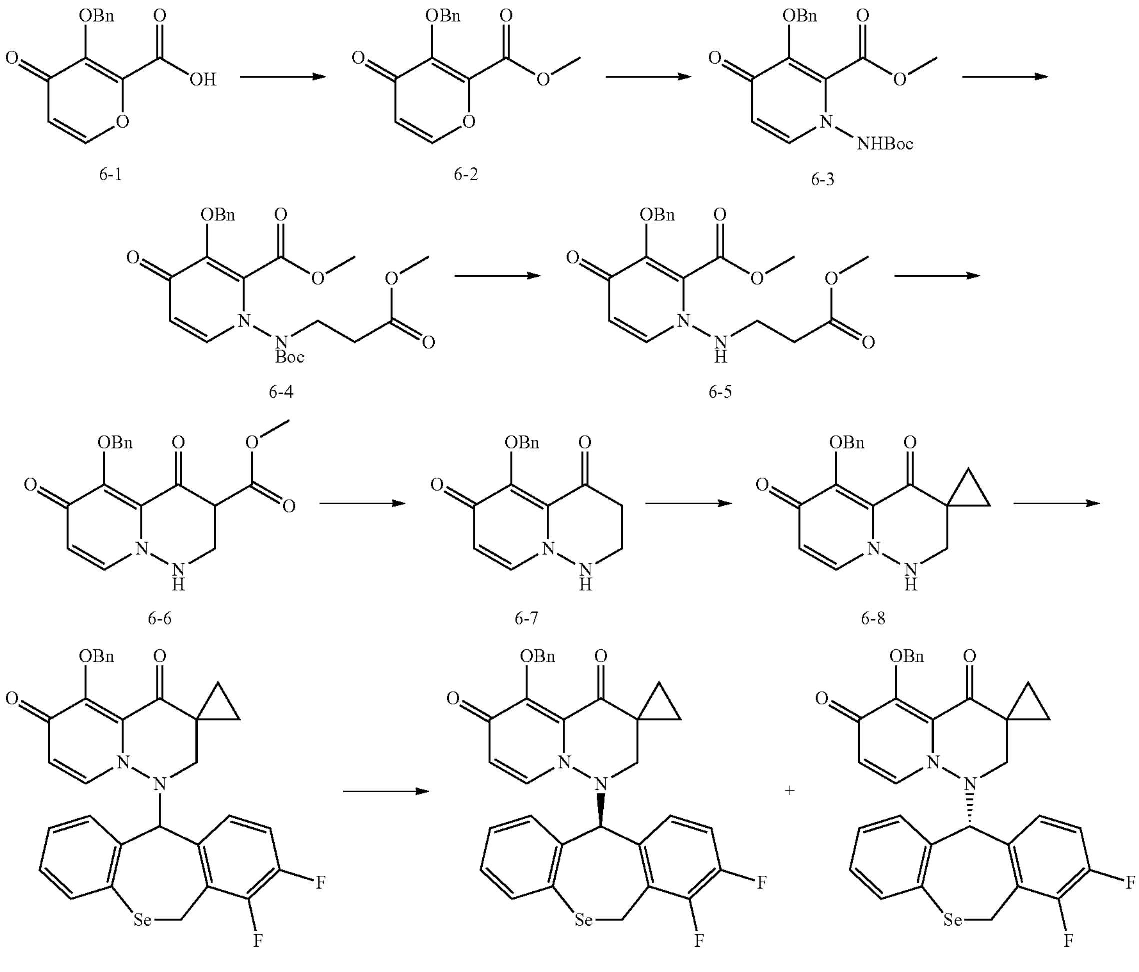
6-1 6-2 6-3 6-4 6-5 6-6 6-7 6-8 6-9 6-9A or 6-9B + 6-9B or 6-9A -continued

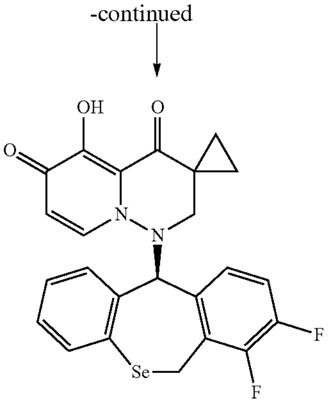

+

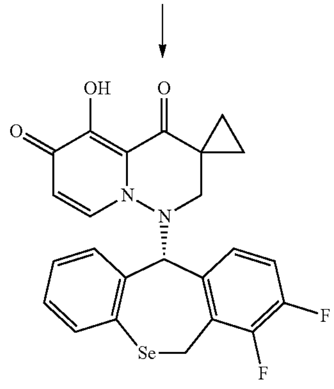

6 or 6′

6′ or 6

Step 1: Synthesis of Compound 6-2

To a methanol (8 mL) and tetrahydrofuran (32 mL) solution of compound 6-1 (3.35 g, 13.61 mmol) was added dropwise a solution of trimethylsilyldiazomethane (2 M, 13.61 mL, 27.22 mmol) under an ice bath. After the dropwise addition was completed, the reaction mixture was warmed to 20° C. and stirred for 1 hour. The reaction mixture was added with saturated citric acid solution (100 mL) and extracted with ethyl acetate (100 mL×3). The organic phases were combined, washed sequentially with saturated sodium bicarbonate solution (100 mL) and saturated brine (100 mL), dried over anhydrous sodium sulfate, filtered, and evaporated to dryness by rotary evaporation to obtain a crude product of compound 6-2, which was directly used in the next reaction step.

Step 2: Synthesis of Compound 6-3

To N,N-dimethylacetamide (80 mL) was added compound 6-2 (3.98 g, 15.29 mmol), tert-butyl carbazate (2.02 g, 15.29 mmol), and pyridinium p-toluenesulfonate (3.84 g, 15.29 mmol). The reaction mixture was then heated to 60° C. and reacted for 12 hours. The reaction mixture was cooled to room temperature, added with water (200 mL), and extracted with ethyl acetate (100 mL×3). The organic phases were combined and washed with water (200 mL) and saturated brine (200 mL) respectively, dried over anhydrous sodium sulfate, filtered, and evaporated to dryness by rotary evaporation. The crude product was purified by silica gel column chromatography (petroleum ether:ethyl acetate=3:1 to 1:2) to obtain compound 6-3.

Step 3: Synthesis of Compound 6-4

Compound 6-3 (2.7 g, 7.21 mmol), methyl acrylate (1.24 g, 14.42 mmol, 1.30 mL), and N,N-diisopropylethylamine (2.80 g, 21.64 mmol, 3.77 mL) were dissolved in acetonitrile (35 mL), and the reaction mixture was stirred at 50° C. for 12 hours. The reaction mixture was evaporated to dryness by rotary evaporation, and the crude product was purified by silica gel column chromatography (petroleum ether:ethyl acetate=4:1 to 1:2, v/v) to obtain compound 6-4.

Step 4: Synthesis of Compound 6-5

To an ethyl acetate (20 mL) solution of compound 6-4 (1.6 g, 3.47 mmol) was added an ethyl acetate solution of hydrochloric acid (4 M, 10 mL). The reaction mixture was stirred at 25° C. for 1 hour. The reaction mixture was then concentrated under reduced pressure to obtain a crude product of compound 6-5 hydrochloride, which was directly used in the next reaction step.

Step 5: Synthesis of Compound 6-6

To acetonitrile (20 mL) was added compound 6-5 (1.18 g, hydrochloride) and potassium tert-butoxide (955.32 mg, 8.51 mmol). The reaction mixture was stirred at 25° C. for 1 hour. The reaction mixture was added with methanol (30 mL), concentrated, and evaporated to dryness by rotary evaporation. The crude product was purified by silica gel column chromatography (petroleum ether:ethyl acetate=3:1 to 0:1, v/v, then dichloromethane:methanol=10:1 to 0:1) to obtain compound 6-6.

Step 6: Synthesis of Compound 6-7

Compound 6-6 (3 g, 9.14 mmol) was dissolved in dimethyl sulfoxide (30 mL) and water (3 mL). Sodium chloride (1.07 g, 18.27 mmol) was then added thereto, and the reaction mixture was stirred at 90° C. for 12 hours. The reaction mixture was diluted with water (100 mL), and then extracted with dichloromethane (100 mL×3). The organic phase was washed with saturated brine (100 mL×2), dried over anhydrous sodium sulfate, and filtered. The filtrate was then concentrated under reduced pressure. The obtained crude product was purified by silica gel column chromatography (dichloromethane:methanol=1:0 to 10:1) to obtain compound 6-7.

Step 7: Synthesis of Compound 6-8

Compound 6-7 (0.3 g, 1.11 mmol) and diphenyl(vinyl)sulfonium trifluoromethanesulfonate (482.68 mg, 1.33 mmol) were dissolved in dimethyl sulfoxide (3.6 mL). Then, 1,8-diazabicyclo[5.4.0]undec-7-ene (506.93 mg, 3.33 mmol) was added thereto. The reaction mixture was stirred at 25° C. for 1 hour. The reaction mixture was diluted with water (30 mL), and then extracted with ethyl acetate (30 mL×3). The organic phase was washed with saturated brine (30 mL×2), dried over anhydrous sodium sulfate. The filtrate was then concentrated under reduced pressure. The obtained crude product was purified by silica gel column chromatography (dichloromethane:methanol=1:0 to 10:1) to obtain compound 6-8. MS (ESI) m/z: 297.3 $[M+H]^+$.

Step 8: Synthesis of Compound 6-9

To ethyl acetate (2 mL) was added compound 6-8 (70 mg, 236.23 μmol) and compound 2-5 (73.51 mg, 236.23 μmol), then added propylphosphonic anhydride (50% ethyl acetate solution, 300.66 mg, 472.46 μmol, 280.99 μL) and methanesulfonic acid (22.70 mg, 236.23 μmol, 16.82 μL). The reaction mixture was stirred at 77° C. for 3 hours. The reaction mixture was cooled to room temperature, added with water (10 mL), and extracted with ethyl acetate (5 mL×2). The organic phases were combined and washed with saturated brine (5 mL), dried over anhydrous sodium sulfate, and filtered. The filtrate was concentrated to dryness under reduced pressure to obtain a crude product. The crude product was purified by a flash silica gel column (dichloromethane:methanol=1:0 to 10:1) to obtain compound 6-9. MS (ESI) m/z: 591.1 $[M+H]^+$.

Step 9: Synthesis of Compound 6-9A and 6-9B

Compound 6-9 was detected by supercritical fluid chromatography (analytical method: column type: CHIRALCEL OD-3 (100 mm×4.6 mm, 3 μm); mobile phase: [A: carbon dioxide, B: 0.05% diethylamine/ethanol]; gradient: B %: increased from 5% to 40% within 4 minutes, maintained for 2.5 minutes; then maintained at 5% for 1.5 minutes) and analyzed as a racemic compound. Compound 6-9A (retention time of 4.024 min) and compound 6-9B (retention time of 4.447 min) were obtained through chiral separation (column type: DAICEL CHIRALCEL OD-H (25 mm×30 mm, 5 μm); mobile phase: [A: carbon dioxide, B: 0.1% ammonia water/ethanol]; gradient: B %: 40%-40%).

Step 10: Synthesis of Compound 6

To N,N-dimethylacetamide (1 mL) was added compound 6-9A (20 mg, 33.93 μmol), then added lithium chloride (7.19 mg, 169.64 μmol), and the reaction mixture was stirred at 80° C. for 12 hours. The reaction mixture was cooled to room temperature and diluted with acetonitrile (2 mL). The crude product was purified by preparative HPLC (column type: Xtimate C18 100×30 mm×3 μm; mobile phase: [water (0.225% formic acid)-acetonitrile]; acetonitrile %: 50% to 70%, 5 minutes) to obtain compound 6. $^1H$ NMR (400 MHz, deuterated methanol) δ 7.59 (d, J=7.53 Hz, 1H), 7.19-7.31 (m, 2H), 7.03-7.19 (m, 2H), 6.90 (br s, 2H), 5.86 (d, J=7.53 Hz, 1H), 5.45-5.61 (m, 2H), 4.26 (br d, J=15.06 Hz, 1H), 4.11 (d, J=12.55 Hz, 1H), 3.07 (br d, J=15.06 Hz, 1H), 1.84-1.97 (m, 1H), 1.60-1.75 (m, 1H), 0.92-1.12 (m, 2H); MS (ESI) m/z: 501.2 $[M+H]^+$.

Step 11: Synthesis of Compound 6'

To N,N-dimethylacetamide (1 mL) was added compound 6-9B (20.00 mg, 33.93 μmol), then added lithium chloride (7.19 mg, 169.64 μmol, 3.47 μL), and the reaction mixture was stirred at 80° C. for 12 hours. The reaction mixture was cooled to room temperature and diluted with acetonitrile (2 mL). The crude product was purified by preparative HPLC (column type: Xtimate C18 100×30 mm×3 μm; mobile phase: [water (0.225% formic acid)-acetonitrile]; acetonitrile %: 50% to 70%, 5 minutes) to obtain compound 6'. $^1H$ NMR (400 MHz, deuterated methanol) δ 7.59 (d, J=7.53 Hz, 1H), 7.19-7.32 (m, 2H), 7.02-7.19 (m, 2H), 6.81-6.96 (m, 2H), 5.86 (d, J=7.53 Hz, 1H), 5.44-5.63 (m, 2H), 4.26 (br d, J=15.06 Hz, 1H), 4.11 (d, J=12.55 Hz, 1H), 3.07 (br d, J=15.06 Hz, 1H), 1.81-1.98 (m, 1H), 1.57-1.73 (m, 1H), 0.90-1.14 (m, 2H). MS (ESI) m/z: 501.1 $[M+H]^+$.

Biological Test Data

Experimental Example 1: Influenza Virus Cytopathic Effect (CPE) Assay

The antiviral activity of the compound against influenza virus (IFV) was evaluated by determining the half-maximal effective concentration ($EC_{50}$) value of the compound. Cytopathic effect assay was widely used to determine the protective effect of a compound on virus-infected cells, reflecting the antiviral activity of the compound.

Influenza Virus CPE Assay

MDCK cells were seeded at a density of 2,000 cells per well in a black 384-well cell culture plate, and then cultured in a 37° C., 5% $CO_2$ incubator overnight. The compound was diluted with the Echo555 non-contact nanoliter acoustic liquid handler (4-fold serial dilution, 8 test concentration points) and added to the cell wells. Influenza virus strains A/PR/8/34 (H1N1) were then added to each cell culture well at 1 to 2 90% tissue culture infectious dose (TCID90), with a final DMSO concentration of 0.5% in the culture medium. Virus control wells (with DMSO and virus, no compound), cell control wells (with DMSO, no compound and virus), and culture medium control wells (with only culture medium, no cells) were set up. The cytotoxicity assay of the compound was carried out in parallel with the antiviral activity assay, with the same experimental conditions except for the absence of the virus. Cell plates were cultured in a 37° C., 5% $CO_2$ incubator for 5 days. After 5 days of culture, CCK8 cell viability assay kit was used to detect cell activity. Original data was used for calculating the antiviral activity and cytotoxicity of the compound.

The antiviral activity and cytotoxicity of the compounds were represented by the inhibition rate (%) of the cellular viral effect caused by the virus, respectively. The calculation formula is as follows:

$$\%\ \text{inhibition rate} = \left(\frac{\text{sample value} - \text{virus control } avg.}{\text{cell control } avg. - \text{virus control } avg.}\right) \times 100$$

The inhibition rate and cytotoxicity of the compound were analyzed using non-linear regression using GraphPad Prism software to obtain the $EC_{50}$ value of the compound. Experimental results are shown in Table 3.

TABLE 3

Inhibition activity of compounds against influenza virus A/PR/8/34 (H1N1)

| Compound | $EC_{50}$ (nM) |
|---|---|
| Compound 2 | 2.0 |
| Compound 2' | 54.5 |
| Compound 3 | 2.8 |
| Compound 3' | 157 |
| Compound 6' | 0.75 |

Conclusion: The compounds of the present disclosure demonstrate a positive effect in inhibiting influenza virus replication at the cellular level.

Experimental Example 2: In Vivo Pharmacodynamic Study

Experimental purpose: To evaluate the efficacy of the compound in a mouse infection model of influenza A H1N1.

Experimental protocol: Mice were infected with the influenza A virus A/PR/8/34 (H1N1) via intranasal instillation. 48 hours after infection, treatment with the compounds commenced, administered orally for a consecutive 7 days, twice daily. The compound's anti-influenza A H1N1 effects in this model were evaluated by observing changes in mouse weight and survival rates.

The experiment used BALB/c mice of SPF grade, 6 to 7 weeks old, female. The mice were allowed to acclimate for at least 3 days in a BSL-2 animal facility before starting the experiment. Day 0 was designated as the day of infection. Mice were anesthetized with an intraperitoneal injection of pentobarbital sodium (75 mg/kg, 10 mL/kg) and, once the mice entered a deeply anesthetized state, the mice were infected intranasally with the A/PR/8/34 (H1N1) virus, with an infection volume of 50 μL. From day 2 to day 8, the test compound was administered orally at 5 mg/kg (administration volume of 10 mL/kg) twice daily. The time of first administration was 48 hours after infection. The state of the mice was observed daily, with weight and survival rates recorded. On day 14, all surviving animals were euthanized.

Experimental Results:

Animal survival rates and weight loss rates were measured, weight loss rate=[(weight on day 0–weight on day N)/weight on day 0]*100%. The results are shown in Table 4: Compound 5 achieved a maximum weight loss rate of 13.77% on Day 7, then the weight began to recover, and the survival rate of mice was 100% by the end of the experiment. Compound 4 achieved a maximum weight loss rate of 7.03% on day 3, then the weight began to recover, and the survival rate of mice was 100% by the end of the experiment.

TABLE 4

Results of animal survival rate and weight loss rate

| Compound | Maximum rate of weight loss (day N) | Survival rate (percentage) |
|---|---|---|
| Compound 5 | 13.77% (Day 7) | 100% |
| Compound 4 | 7.03% (Day 3) | 100% |

Conclusion: The compounds of the present disclosure show excellent weight protection in an in vivo pharmacodynamic model, and the recovery begins early.

Experimental Example 3: Cytopathic Effect (CPE) Assay of Baloxavir-Resistant A/PR/8/34 (H1N1) I38T Influenza Virus Strain Experimental purpose: To evaluate the antiviral activity of the compound against the Baloxavir-resistant A/PR/8/34 (H1N1) I38T influenza virus strain by determining the half-maximal effective concentration ($EC_{50}$) of the compounds.

Experimental protocol: MDCK cells were seeded at a density of 15,000 cells per well in a 96-well cell culture plate and cultured overnight in a 37° C., 5% $CO_2$ incubator. The next day, the compound solution (3-fold serial dilutions, 8 concentration points, three replicate wells) and the Baloxavir-resistant A/PR/8/34 (H1N1) influenza virus strain were added. The final concentration of DMSO in the cell culture medium was 0.5%. The cells were cultured in a 5% $CO_2$, 37° C. incubator for 5 days, until the cell pathogenicity in the virus-infected control well without the compound reached 80 to 95%. Then the cell viability in each well was detected using CCK8. If the cell viability in the wells containing the compound was higher than that in the virus-infected control wells, that is, the CPE was weakened, then the inhibitory effects of the compound on the tested virus could be validated.

Experimental Results:

The antiviral activity of the compounds was represented by the inhibitory activity (%) of the compound on the cellular viral effect caused by the virus. The calculation formula is as follows:

$$\%\ \text{inhibition activity} = \left(\frac{\text{sample value} - \text{virus control } avg.}{\text{cell control } avg. - \text{virus control } avg.}\right) \times 100$$

$EC_{50}$ was acquired by performing non-linear regression analysis on the inhibitory activity and cell viability of the compounds using GraphPad Prism (version 5) software. The method chosen for curve fitting was "log(inhibitor) vs. response—variable slope". Experimental results are shown in Table 5.

TABLE 5

Results of inhibition activity of the compounds of the present disclosure against Baloxavir-resistant A/PR/8/34 (H1N1) I38T influenza virus strain

| Compound | $EC_{50}$ (nM) |
|---|---|
| Compound 2 | 133.7 |
| Compound 3 | 57.5 |

Conclusion: The compounds of the present disclosure demonstrate positive effects in inhibiting the replication of Baloxavir-resistant A/PR/8/34 (H1N1) influenza virus strain at the cellular level.

Experimental Example 4: In Vivo Pharmacodynamic Study

Experimental purpose: To evaluate the efficacy of the compound in a mouse infection model of influenza A virus H1N1 drug-resistant strain.

Experimental protocol: Mice were infected with influenza A virus Baloxavir-resistant A/PR/8/34 (H1N1) I38T virus strain via intranasal instillation. 2 hours before infection, treatment with the compounds commenced, administered orally for a consecutive 7 days, twice daily. The compound's anti-influenza A virus H1N1 effects in this model were evaluated by observing changes in mouse weight and survival rates.

The experiment used BALB/c mice of SPF grade, 6 to 7 weeks old, female. The mice were allowed to acclimate for at least 3 days in a BSL-2 animal facility before starting the experiment. Day 0 was designated as the day of infection. After being deeply anesthetized by intraperitoneal injection of Zoletil 50/Xylazine hydrochloride, mice were intranasally infected with the Baloxavir-resistant A/PR/8/34 (H1N1) I38T virus strain, with an infection volume of 50 μL. From day 2 to day 8, the test compound was administered orally at 15 mg/kg or 50 mg/kg (administration volume of 10 mL/kg) twice daily. The time of first administration was 2 hours before infection. The mice were observed daily, with weight and survival rates recorded. On day 14, all surviving animals were euthanized.

Experimental Results:

Animal survival rates and weight loss rates were measured, weight loss rate=[(weight on day 0–weight on day N)/weight on day 0]*100%. Experimental results are shown in Table 6. When compound 4 was administered at a dose of 50 mg/kg, the body weight of the mice hardly decreased, and the survival rate of the mice was 100% by the end of the experiment.

TABLE 6

| Results of animal survival rate and weight loss rate | | | |
|---|---|---|---|
| Compound | Dose | Maximum rate of weight loss (day N) | Survival rate (%) |
| Compound 4 | 15 mg/kg | 5.6% (Day 7) | 100% |
| | 50 mg/kg | 0.6% (Day 3) | 100% |

Conclusion: The compounds of the present disclosure show excellent weight protection in an in vivo pharmacodynamic model, and the recovery begins early.

Experimental Example 5: Plasma Protein Binding Rate Test of Compounds

Experimental purpose: To evaluate the protein binding rate of the compounds of the present disclosure in the plasma of CD-1 mouse, SD rat, and human using equilibrium dialysis.

Experimental protocol: The test compounds were diluted with dialysis buffer into the plasma of the above five species to prepare samples with a final concentration of 2 μM. The samples were then added to a 96-well equilibrium dialysis device and dialyzed using phosphate buffer solution at 37° C. for 4 hours. Warfarin was used as a control compound in the experiment. The concentration of the test compounds and warfarin in the plasma and buffer was determined using LC-MS/MS.

Experimental results: The results are shown in Table 7.

TABLE 7

| Results of plasma protein binding rate of the compounds of the present disclosure | |
|---|---|
| Compound | Plasma protein binding (PPB) unbound (%) |
| Compound 3 | 25.9(H), 31.3(R), 13.7(M), 24.6(D), 31.6(C) |
| Compound 2 | 6.7(H), 7.9(R), 9.5(M), 13.6(D), 13.6(C) |

Note: H stands for human, R stands for rat, M stands for mouse, D stands for dog, C stands for crab-eating macaque.

Conclusion: The compounds of the present disclosure have moderate plasma protein binding rates in the plasma of the five species, which indicates that in the plasma of the above five species, the test compounds have moderate free drug concentration ratios, and have good druggability.

Experimental Example 6: Pharmacokinetic Study in Rats

Experimental purpose: To investigate the plasma pharmacokinetics of the compounds of the present disclosure in male SD rats after a single intravenous injection or an oral administration.

Experimental animals: male SD rats, 6 to 8 weeks old, weighing between 200 to 300 g;

Experimental procedure: Injection administration (i.v.) was carried out with a dose of 1 mpk, at a concentration of 0.50 mg/mL, with a vehicle of 40% DMAC+40% PG+20% (20% HP-β-CD+water). Oral administration (po) was carried out with a dose of 10 mpk, at a concentration of 1 mg/mL, with a vehicle of 3% DMSO+10% solutol HS+87% water.

Sample collection: At each time point, 0.03 mL of blood samples were collected from the experimental animals through a puncture of the saphenous vein. The actual blood collection time was recorded. All blood samples were kept in commercially available 1.5 mL EDTA-K2 anticoagulant tubes. After blood sample collection, DDV was added into the plasma matrix as a stabilizer, wherein the ratio of plasma to Dichlorvos (DDV) solution was 40:1. The DDV solution was a 40 mM DDV solution in acetonitrile/water (1:1). Within half an hour, the mixture was centrifuged at 4° C. and 3000 g for 10 minutes. The supernatant plasma was aspirated, quickly placed in dry ice, and stored in a −80° C. refrigerator for LC-MS/MS analysis.

Data analysis: A non-compartmental model in Phoenix WinNonlin 6.3 pharmacokinetic software was used to process the plasma concentration data. The pharmacokinetic parameters were calculated using the linear-log trapezoidal method: Cl (apparent clearance rate), $T_{1/2}$ (the time required to clear half of the compound), $C_{max}$ (peak concentration), and $AUC_{0\text{-}last}$ (integral area under the concentration-time curve from 0 to the last sampling time). The results are shown in Table 8.

TABLE 8

| PK results of compounds of the present disclosure in rats | | | | |
|---|---|---|---|---|
| Compound | Cl (mL/Kg/min) | $T_{1/2}$ (h) | $C_{max}$ (nM) | $AUC_{0\text{-}last}$ (nM · h) |
| Compound 3 (i.v.) | 178 | 1.7 | / | 171 |
| Compound 4 (po) | / | 2.9 | 332 | 946 |

Experimental conclusion: The compounds of the present disclosure have high plasma exposure when administered orally, indicating good pharmacokinetic properties.

Experimental Example 7: Pharmacokinetic Study in Beagle Dogs

Experimental purpose: To investigate the plasma pharmacokinetics of the compounds of the present disclosure in male beagle dogs after a single intravenous injection or an oral administration.

Experimental animals: male beagle dogs, >6 months old, weighing between 6 to 12 kg.

Experimental procedure: Injection administration (i.v.) was carried out with a dose of 1 mpk, at a concentration of 1 mg/mL, with a vehicle of 10% DMAC+90% (20% HP-β-CD+water). Oral administration (po) was carried out with a dose of 10 mpk, at a concentration of 2 mg/mL, with a vehicle of 3% DMSO+10% solutol HS+87% water.

Sample collection: At each time point, 0.8 mL of blood samples were collected from the experimental animals through a puncture of the saphenous vein. The actual blood collection time was recorded. All blood samples were kept in commercially available 1.5 mL EDTA-K2 anticoagulant tubes. After blood sample collection, DDV was added into the plasma matrix as a stabilizer, wherein the ratio of plasma to Dichlorvos (DDV) solution was 40:1. The DDV solution was a 40 mM DDV solution in acetonitrile/water (1:1). Within half an hour, the mixture was centrifuged at 4° C. and 3000 g for 10 minutes. The supernatant plasma was aspirated, quickly placed in dry ice, and stored in a −80° C. refrigerator for LC-MS/MS analysis.

Data analysis: A non-compartmental model in Phoenix WinNonlin 6.3 pharmacokinetic software was used to process the plasma concentration data. The pharmacokinetic parameters were calculated using the linear-log trapezoidal method: Cl, $T_{1/2}$, $C_{max}$, and $AUC_{0\text{-}last}$. The results are shown in Table 9.

TABLE 9

PK results of compounds of the present disclosure in beagle dogs

| Compound | Cl (mL/Kg/min) | $T_{1/2}$ (h) | $C_{max}$ (nM) | $AUC_{0\text{-}last}$ (nM · h) |
|---|---|---|---|---|
| Compound 3 (i.v.) | 36.8 | 3.7 | / | 830 |
| Compound 4 (po) | / | 6.4 | 1100 | 3852 |

Experimental conclusion: The compounds of the present disclosure have a low clearance rate, a long half-life, and high plasma exposure when administered orally, indicating good pharmacokinetic properties.

What is claimed is:

1. A compound of formula (VI) or a pharmaceutically acceptable salt thereof,

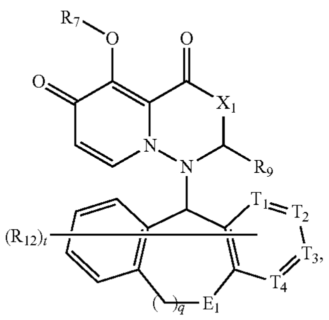

(VI)

wherein $R_7$ is selected from H and

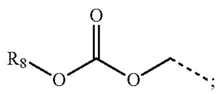

;

$R_8$ is selected from $C_{1-3}$ alkyl and

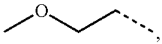

, and the $C_{1-3}$ alkyl and

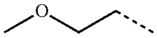

are optionally substituted by 1, 2, or 3 $R_a$;

$R_9$ is selected from H, $E_1$ is selected from Se, $X_1$ is selected from $CR_{10}R_{11}$, and $R_{10}$ and $R_{11}$ together with the atom to which they are commonly connected form a $C_{3-5}$ cycloalkyl group;

alternatively, $X_1$ and $R_9$ together with the atom to which they are connected form

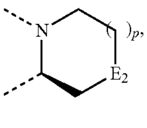

, p is selected from 0 and 1, one of $E_1$ and $E_2$ is selected from Se, and the other is selected from S and O;

each $R_{12}$ is independently selected from H, F, Cl, Br, I, OH, $NH_2$, —COOH, $C_{1-3}$ alkyl, $C_{1-3}$ alkoxy, and $C_{1-3}$ alkylamino, and the $C_{1-3}$ alkyl, $C_{1-3}$ alkoxy, and $C_{1-3}$ alkylamino are independently substituted by 1, 2, or 3 $R_b$;

$T_1$, $T_2$, $T_3$, and $T_4$ are each independently selected from CH and N;

q is selected from 0 and 1;

t is selected from 0, 1, 2, 3, and 4;

each $R_a$ and $R_b$ is independently selected from H, F, Cl, Br, and I;

provided that when $T_1$ is selected from CH, $E_1$ is selected from Se, $E_2$ is selected from O, p is selected from 1, and q is selected from 1, each $R_{12}$ is independently selected from OH and $NH_2$.

2. The compound or the pharmaceutically acceptable salt thereof according to claim 1, wherein each $R_{12}$ is independently selected from F.

3. The compound or the pharmaceutically acceptable salt thereof according to claim 1, wherein $R_8$ is selected from $CH_3$, $CH_2CH_3$, $CH_2CH_2CH_3$, $CH(CH_3)_2$, and

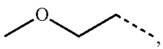

, and the $CH_3$, $CH_2CH_3$, $CH_2CH_2CH_3$, $CH(CH_3)_2$, and

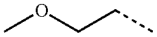

are optionally substituted by 1, 2, or 3 $R_a$.

4. The compound or the pharmaceutically acceptable salt thereof according to claim 3, wherein $R_8$ is selected from $CH_3$, $CH_2CH_3$, $CH(CH_3)_2$, and

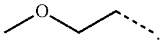

.

5. The compound or the pharmaceutically acceptable salt thereof according to claim 1, wherein $R_7$ is selected from H,

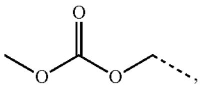

,

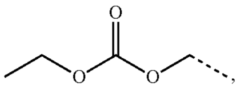

,

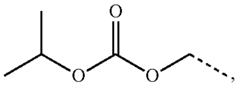

, and

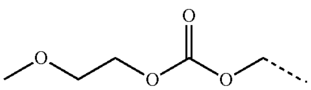

.

6. The compound or the pharmaceutically acceptable salt thereof according to claim 1, wherein $E_1$ is selected from Se and $E_2$ is selected from O.

7. The compound or the pharmaceutically acceptable salt thereof according to claim 1, wherein the structural moiety

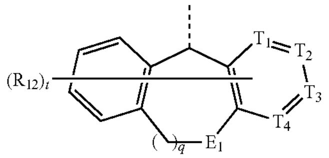

is selected from

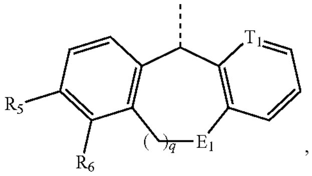, $R_5$ and $R_6$ are each independently selected from H, F, Cl, Br, I, OH, $NH_2$, —COOH, $C_{1-3}$ alkyl, $C_{1-3}$ alkoxy, and $C_{1-3}$ alkylamino, and the $C_{1-3}$ alkyl, $C_{1-3}$ alkoxy, and $C_{1-3}$ alkylamino are each independently and optionally substituted by 1, 2, or 3 $R_b$.

8. The compound or the pharmaceutically acceptable salt thereof according to claim 7, wherein the structural moiety

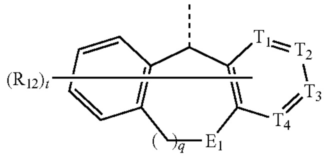

is selected from

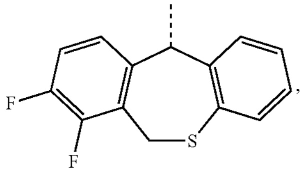,

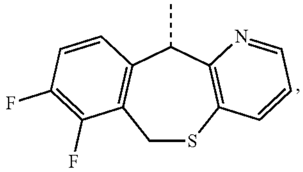,

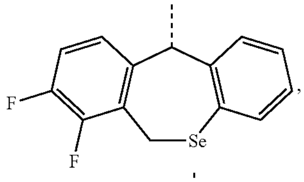, and

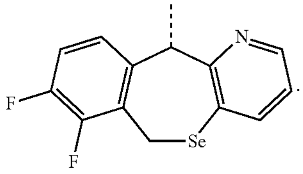.

9. The compound or the pharmaceutically acceptable salt thereof according to claim 1, wherein the structural moiety

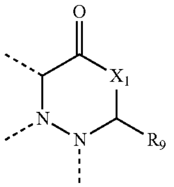

is selected from

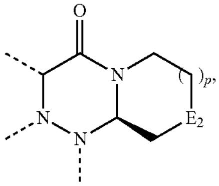

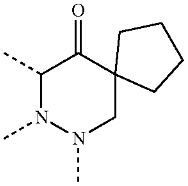, 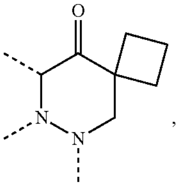, and

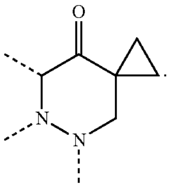.

10. The compound or the pharmaceutically acceptable salt thereof according to claim 9, wherein the structural moiety

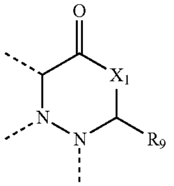

is selected from

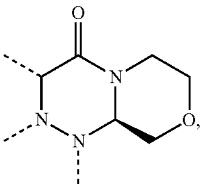 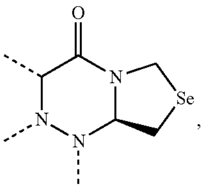,

-continued

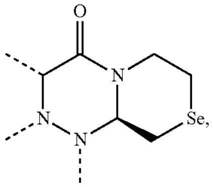

and

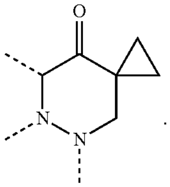

.

11. The compound or the pharmaceutically acceptable salt thereof according to claim 1, selected from, (V)

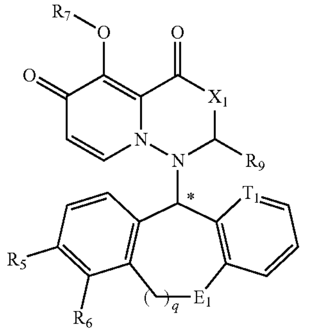

wherein $R_5$ and $R_6$ are each independently selected from H, F, Cl, Br, I, OH, and $NH_2$;

$R_7$ is selected from H and

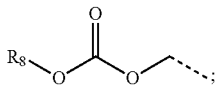

;

$R_8$ is selected from $C_{1-3}$ alkyl and

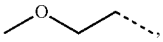

, and the $C_{1-3}$ alkyl and

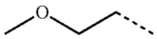

are optionally substituted by 1, 2, or 3 $R_a$;

$R_9$ is selected from H, $E_1$ is selected from Se, $X_1$ is selected from $CR_{10}R_{11}$, and $R_{10}$ and $R_{11}$ together with the atom to which they are commonly connected form the $C_{3-5}$ cycloalkyl group;

alternatively, $X_1$ and $R_9$ together with the atom to which they are connected form

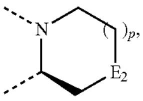

one of $E_1$ and $E_2$ is selected from Se, and the other is selected from S and O;

$T_1$ is selected from CH and N;

p and q are each independently selected from 0 and 1;

each $R_a$ is independently selected from H, F, Cl, Br, and I;

provided that when $T_1$ is selected from CH, $E_1$ is selected from Se, $E_2$ is selected from O, p is selected from 1, and q is selected from 1, $R_5$ and $R_6$ are each independently selected from OH and $NH_2$;

the carbon atom with "*" is a chiral carbon atom, which exists in the form of (R) or (S) single enantiomer or in an enantiomer-enriched form.

12. The compound or the pharmaceutically acceptable salt thereof according to claim 11, selected from, (IV)

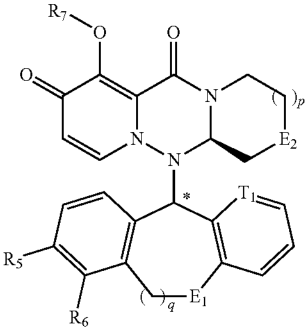

and (V-1)

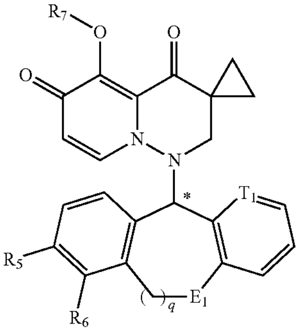

, wherein the carbon atom with "*" is a chiral carbon atom, which exists in the form of (R) or (S) single enantiomer or in an enantiomer-enriched form.

13. The compound or the pharmaceutically acceptable salt thereof according to claim 12, selected from, (IV-A)

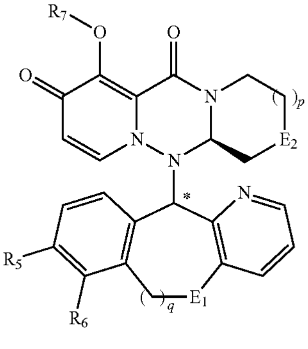

and

-continued (V-1-A)

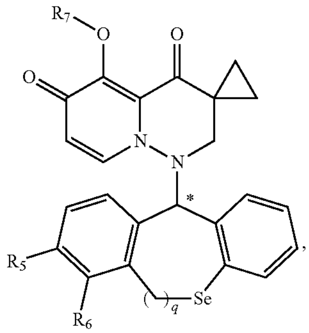
, wherein the carbon atom with "*" is a chiral carbon atom, which exists in the form of (R) or (S) single enantiomer or in an enantiomer-enriched form.

14. The compound or the pharmaceutically acceptable salt thereof according to claim 13, selected from, (III-1)

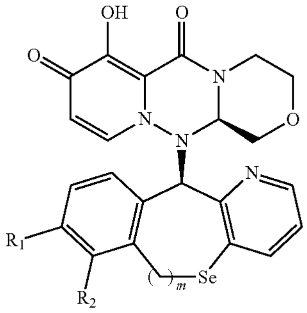

(III-2)

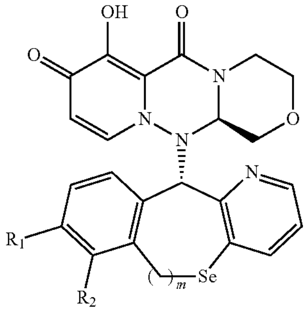

(IV-1)

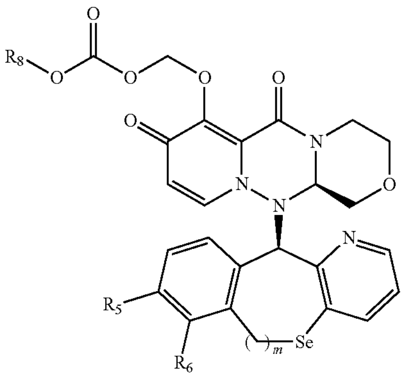

-continued (IV-2)

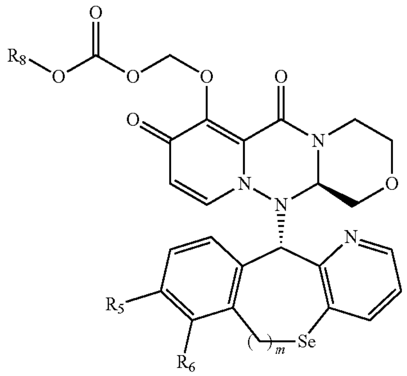

(V-A-1)

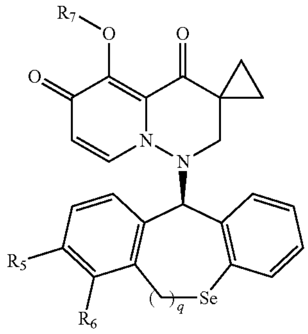
and (V-A-2)

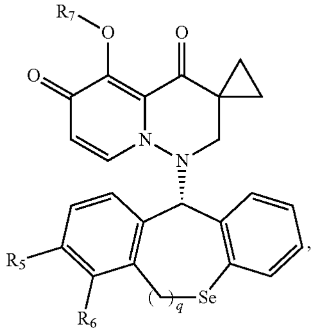
, wherein $R_1$, and $R_2$ are each independently selected from H, F, Cl, Br, I, OH, and $NH_2$;

m is selected from 0 and 1.

15. The compound or the pharmaceutically acceptable salt thereof according to claim 14, wherein $R_1$ and $R_2$ are each independently selected from F.

16. The compound or the pharmaceutically acceptable salt thereof according to claim 14, wherein $R_5$ and $R_6$ are each independently selected from F.

17. The compound or the pharmaceutically acceptable salt thereof according to claim 14, selected from,
(III-1a)
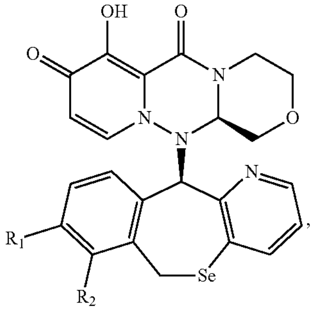
(III-1b)
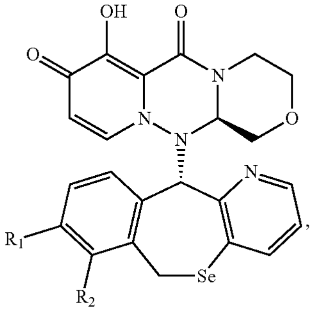
(IV-1a)
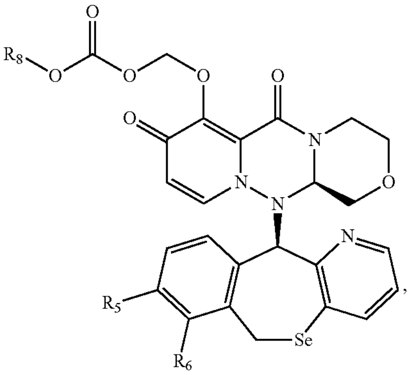
(IV-1b)
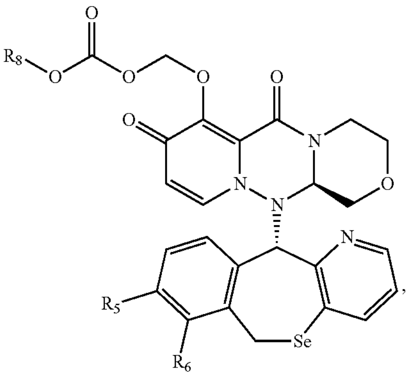
-continued
(V-1a)
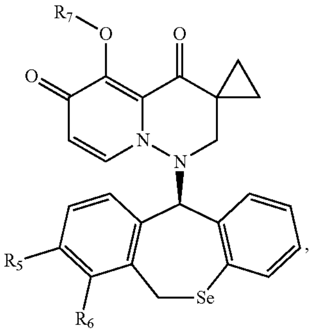
and
(V-1b)
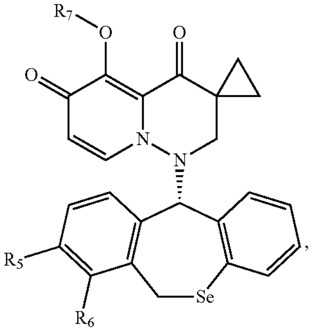
18. A compound of the following formula or a pharmaceutically acceptable salt thereof, selected from
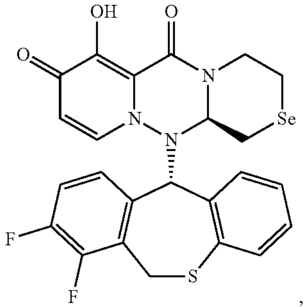
,
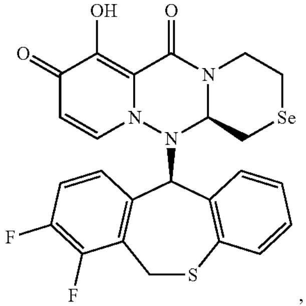
, -continued

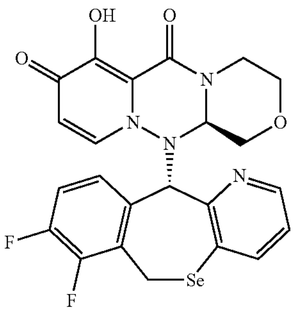

,

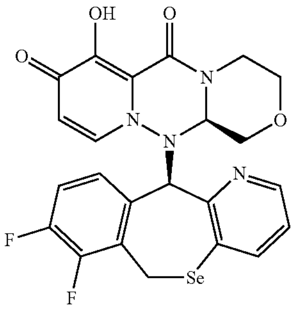

,

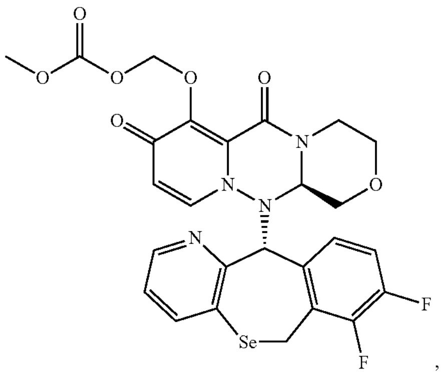

,

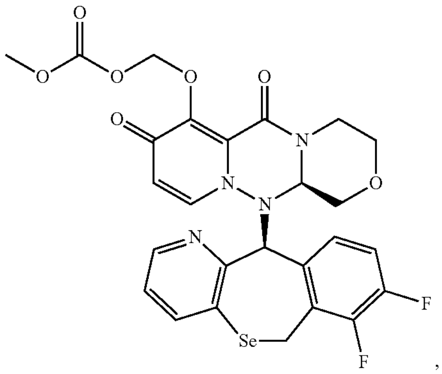

,

-continued

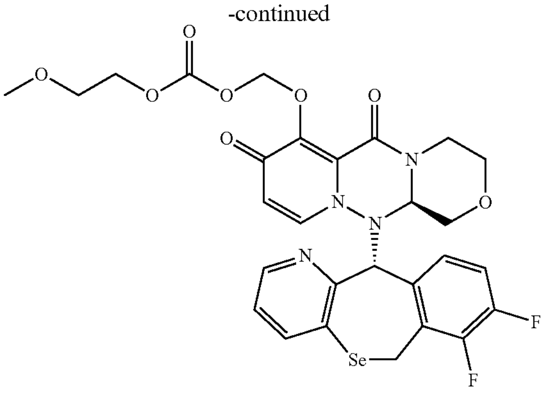

,

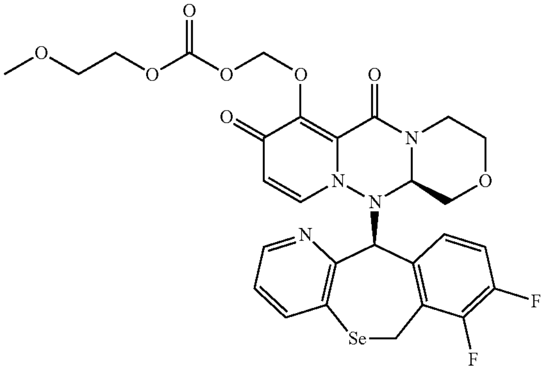

,

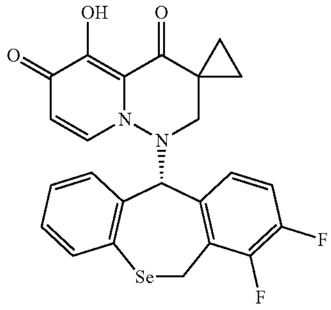

, and

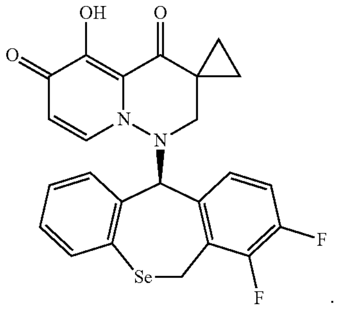 [SMILES: O=C1c2c(O)c(=O)ccn2N([C@@H]2c3ccccc3[Se]Cc3c2ccc(F)c3F)CC12CC2]

.

19. A method for treating influenza virus in a subject in need thereof, comprising: administering the compound or the pharmaceutically acceptable salt thereof according to claim 1 to the subject.

20. A method for treating influenza virus in a subject in need thereof, comprising: administering the compound or the pharmaceutically acceptable salt thereof according to claim 18 to the subject.

* * * * *